US00RE36256E

United States Patent [19]

Spada et al.

[11] E Patent Number: Re. 36,256

[45] Reissued Date of Patent: Jul. 20, 1999

[54] BIS MONO- AND BICYCLIC ARYL AND HETEROARYL COMPOUNDS WHICH INHIBIT EGF AND/OR PDGF RECEPTOR TYROSINE KINASE

[75] Inventors: Alfred P. Spada, Lansdale; Michael R. Myers, Reading; Martin P. Maguire, Mont Clare; Paul E. Persons, King of Prussia, all of Pa.

[73] Assignee: Rhone-Poulenc Rorer Pharmaceuticals, Inc., Collegeville, Pa.

[ * ] Notice: This patent is subject to a terminal disclaimer.

[21] Appl. No.: 08/988,005

[22] Filed: Dec. 10, 1997

Related U.S. Patent Documents

Reissue of:

[64] Patent No.: 5,480,883
Issued: Jan. 2, 1996
Appl. No.: 08/166,199
Filed: Dec. 10, 1993

U.S. Applications:

[62] Continuation-in-part of application No. 07/988,515, Dec. 10, 1992, abandoned, and a continuation-in-part of application No. 08/146,072, Nov. 8, 1993, Pat. No. 5,409,930, which is a continuation-in-part of application No. PCT/US92/03736, May 6, 1992, abandoned, which is a continuation-in-part of application No. 07/698,420, May 10, 1991, abandoned, said application No. 07/988,515, filed as application No. PCT/US92/03736, is a continuation-in-part of application No. 07/698,420.

[51] Int. Cl.[6] ..... A61K 31/495; A61K 31/535; C07D 241/52; C07D 241/54

[52] U.S. Cl. ..... 514/249; 514/234.8; 544/353; 544/354; 544/356

[58] Field of Search ..... 544/353, 354, 544/356; 514/234.8, 249, 353

[56] References Cited

U.S. PATENT DOCUMENTS

| | | | |
|---|---|---|---|
| 3,715,358 | 2/1973 | Witzel et al. | 514/327 |
| 3,718,743 | 2/1973 | Shen et al. | 514/327 |
| 3,985,749 | 10/1976 | Foster | 544/293 |
| 4,322,420 | 3/1982 | Kobayashi et al. | 514/259 |
| 4,464,375 | 8/1984 | Kobayashi et al. | 514/259 |
| 4,465,686 | 8/1984 | Lesher et al. | 514/345 |
| 4,599,423 | 7/1986 | Lesher et al. | 546/300 |
| 4,661,499 | 4/1987 | Young et al. | 514/311 |
| 5,134,148 | 7/1992 | Crawley et al. | 514/312 |
| 5,409,930 | 4/1995 | Spada et al. | 514/248 |

FOREIGN PATENT DOCUMENTS

| | | |
|---|---|---|
| 9331010 | 1/1993 | Australia . |
| 0520722 | 12/1992 | European Pat. Off. . |
| 1543560 | 4/1979 | United Kingdom . |
| 9220642 | 11/1992 | WIPO . |

OTHER PUBLICATIONS

Tamao et al., "Nickel–Phosphine Complex–Catalyzed . . . ", Tetrahedron, vol. 38, No. 22, pp. 3347–3354, 1982.

Yamamoto et al., "General Method for Synthesis of Bipyridines: Palladium . . . ", Synthesis, pp. 564–565, 1986.

Yamamoto et al., "Studies on Organometallic Compounds. III. Reaction of . . . ", Chem. Pharm. Bull., vol. 30, No. 6, pp. 2003–2010, 1982.

Ishikura et al., "A Simple & Regioselective Preparation of 2–or 3–. . . ", Heterocycles, vol. 23, No. 9, pp. 2375–2386, 1985.

Stem et al., "Potential–Dependent Surface Chemistry of . . . ", J. Am. Soc., vol. III. No. 3, pp. 877–891, 1989.

Yoshina, "Quinoline Derivatives", Chemical Abstracts, vol. 84, Abstract #164632t, p. 453, 1976.

Barker et al., "Dehalogenation of 1–Halothienyldi & tetra . . . ", Chemical Abstracts, vol. 103, Abstract #123292z, p. 709, 1985.

Epling et al., "Sulfur–Containing 2–Anylquinoline Methanols . . . ", Chemical Abstracts, vol. 108, Abstract #55860j, 704, 1988.

Beilstein—band EIII/IV 21, p. 2436, 1978.

Saeed et al., "Preparation of Phenylquinoxaline from α, α–diamino . . . ", J. Heterocyclic Chem., vol. 20, pp. 1739–1740, 1983.

*Primary Examiner*—Richard L. Raymond
*Attorney, Agent, or Firm*—Bell, Boyd & Lloyd

[57] ABSTRACT

This invention relates to bis mono- and/or bicyclic aryl and/or heteroaryl compounds exhibiting protein tyrosine kinase inhibition activity. More specifically, it relates to the method of inhibiting abnormal cell proliferation in a patient suffering from a disorder characterized by such proliferation comprising the administration thereto of an EGF and/or PDGF receptor inhibiting effective amount of said bis mono- and/or bicyclic aryl and/or heteroaryl compound and to the preparation of said compounds and their use in pharmaceutical compositions used in this method.

20 Claims, No Drawings

BIS MONO- AND BICYCLIC ARYL AND HETEROARYL COMPOUNDS WHICH INHIBIT EGF AND/OR PDGF RECEPTOR TYROSINE KINASE

Matter enclosed in heavy brackets [ ] appears in the original patent but forms no part of this reissue specification; matter printed in italics indicates the additions made by reissue.

BACKGROUND OF THE INVENTION

[This application is a continuation-in-part application of U.S. Ser. No. 07/988,515 filed Dec. 10, 1992, now abandoned which is a continuation-in-part application of U.S. Ser. No. 07/698,420, filed May 10, 1991 now abandoned and a continuation-in-part application of PCT International Application Ser. No. PCT/US92/03736 filed May 6, 1992.]

*This application is a reissue of 08/166,199, filed Dec. 10, 1993, now U.S. Pat. No. 5,480,883, which, in turn, is a continuation-in-part application of U.S. patent application Ser. No. 07/988,515, filed Dec. 10, 1992, now abandoned, which, in turn, is a continuation-in-part application of International Patent Application No. PCT/US92/03736, filed May 6, 1992, now abandoned, which, in turn, is a continuation-in-part application of U.S. patent application Ser. No. 07/698,420, filed May 10, 1991, now abandoned. This application is also a reissue of 08/166,199, filed Dec. 10, 1993, now U.S. Pat. No. 5,480,883, which, in turn, is a continuation-in-part of U.S. patent application Ser. No. 08/146,072, filed Nov. 8, 1993, now U.S. Pat. No. 5,409,930, which is the National Stage of International Patent Application No. PCT/US92/03736, filed May 6, 1992, now abandoned, which, in turn, is a continuation-in-part application of U.S. patent application Ser. No. 07/698,420, filed May 10, 1991, now abandoned.*

FIELD OF THE INVENTION

This invention relates to the modulation and/or inhibition of cell signaling, cell proliferation, cell inflammatory response, the control of abnormal cell growth and cell reproduction. More specifically, this invention relates to the use of bis mono- and/or bicyclic aryl and/or heteroaryl compounds in inhibiting cell proliferation, including compounds which are useful protein tyrosine kinase (PTK) inhibitors.

Normal cellular reproduction is believed to be triggered by the exposure of the cellular substrate to one or more growth factors, examples of which are insulin, epidermal growth factor (EGF) and platelet-derived growth factor (PDGF). Such growth factor receptors are imbedded in and penetrate through the cellular membrane. The inhibition of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylation enzymes include tyrosine kinases, which catalyze phosphorylation of tyrosine amino acid residues of substrate proteins.

Many disease states that characterized by the uncontrolled reproduction of cells. These disease states involve a variety of cell types and include disorders such as leukemia, cancer, psoriasis, inflammatory disease, bone diseases, atherosclerosis and restenosis occuring subsequent to angioplastic procedures. This inhibition of tyrosine kinase is believed to have utility in the control of uncontrolled cellular reproduction, i.e., cellular proliferative disorders.

Initiation of autophosphorylation, i.e., phosphorylation of the growth factor receptor itself, and of the phosphorylation of a host of intracellular substrates are some of the biochemical events which are involved in mediator release mitogenesis and cell proliferation. Autophosphorylation of the insulin receptor and phosphorylation of substrate proteins by other receptors are the earliest identifiable biochemical hormonal responses.

Elimination of the protein tyrosine kinase (PTK) activity of the insulin receptor and of the epidermal growth factor (EGF) receptor by site-directed mutagenesis of the cellular genetic material which is responsible for generation of insulin and EGF results in the complete elimination of the receptor's biological activity. This is not particularly desirable because insulin is needed by the body to perform other biological functions which are not related to cell proliferation. Accordingly, compounds which inhibit the PTK portion of the EGF and/or PDGF receptor at concentrations less than the concentrations needed to inhibit the PTK portion of the insulin receptor could provide valuable agents for selective treatment of cell proliferation disorders.

REPORTED DEVELOPMENTS

It has been reported that the most potent inhibitors of EGF receptors Inhibit EGF-induced proliferation of A431/clone 15 cells with little or no effect on the proliferation of such cells when induced by other growth factors. It has been reported also that erbstatin inhibits the autophosphorylation of the EGF receptor in membranes of A431 cells. Higher concentrations of erbstatin are required to inhibit cyclic adenosine 3',5'-monophosphate (cAMP)-dependent protein kinase.

SUMMARY OF THE INVENTION

In accordance with the present invention, there is provided a method of inhibiting abnormal cell proliferation in a patient suffering from a disorder characterized by such proliferation comprising the administration to a patient of an EGF and/or PDGF receptor inhibiting effective amount of a bis mono- and/or bicyclic aryl compound exhibiting protein tyrosine kinase inhibition activity wherein each aryl group is a ring system containing 0–4 hetero atoms, said compound being optionally substituted or polysubstituted.

Another aspect of the present invention relates to pharmaceutical compositions comprising, in admixture with a pharmaceutically acceptable carrier, a pharmaceutically effective amount of a compound of the aforementioned type. Another aspect of this invention comprises compounds useful in the practice of the present method.

With respect to the method aspects of this invention, the compounds described by Formula I below constitute a class of the aforementioned bis mono- and/or bicyclic aryl, heteroaryl, carbocyclic or heterocarbocyclic compounds for use in the practice of the present invention:

Formula I

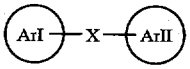

where:

Ar I and Ar II are independently a substituted or unsubstituted mono- or bicyclic ring, said rings optionally substituted with 0 to about 3 R groups; and X is $(CHR_1)_{0-4}$ or $(CHR_1)_m$—Z—$(CHR_1)_n$ where Z is O, NR', S, SO or $SO_2$, m and n are 0–3 and m+n=0–3 and $R_1$ and R' are independently hydrogen or alkyl; or a pharmaceutically acceptable salt thereof.

Preferably, AR I is a substituted or unsubstituted mono- or bicyclic aryl or heteroaryl ring system of about 5 to about 12 atoms and where each monocyclic ring may contain 0 to about 3 hetero atoms, and each bicyclic ring may contain 0 to about 4 hetero atoms selected from N, O and S provided said hetero atoms are not vicinal oxygen and/or sulfur atoms and where the substituents may be located at any appropriate position of the ring system and are described by R.;

Ar II may be as described for Ar I or at least one ring is a substituted or unsubstituted saturated carbocyclic of about 3 to about 7 atoms where each monocyclic ring may contain 0 to about 2 hetero atoms, and each bicyclic ring may contain 0 to about 4 hetero atoms selected from N, O and S provided said hetero atoms are not vicinal oxygen and/or sulfur atoms and where the substituents may be located at any appropriate position of the ring system and are described by R.

Preferred Ar I and Ar II monocyclic aryl or heteroaryl rings include substituted or unsubstituted benzene, pyrrole, thiophene, furan, thiazole, imidazole, pyrazole, 1,2,4-triazole, pyridine, 2(1H)-pyridone, 4(1H)-pyridone, pyrazine, pyrimidine, pyridazine, isothiazole, isoxazole, s-triazine, oxazole and tetrazole.

Preferred Ar II carbomonocyclic rings include substituted and unsubstituted cycloalkanes such as cyclopentane, cyclohexane, cycloheptane and partially unsubstituted cycloalkanes such as cyclopent-1-ene and heteromonocyclic rings such as piperdine, piperazine, morpholine and pyrrolidine.

Preferred Ar I and Ar II bicyclic rings include substituted and unsubstituted bicyclic aryl and heteroaryl rings such as naphthalene, naphthyridine, benzofuran, benzothiophene, indole, 1H-indazole, indoline, benzopyrazole, 1,3-benzodioxole, benzoxazole, purine, coumarin, chromone, quinoline, isoquinoline, benzimidazole, quinazoline, pyrido [2,3-b]pyrazine, pyrido[3,4-b]pyrazine, pyrido[3,2-c] pyridazine, pyrido[3,4-b]-pyridine, pteridine, 2(1H)-quinolone, 1 (2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, or cinnoline.

Preferred Ar II carbobicyclic rings include substituted and unsubstituted bicycloalkanes such as tetralin, decaline and adamantane and preferred heterobicyclic rings such as imidazolidine, chroman, indoline and quinuclidine Preferred R substituents other than hydrogen include alkyl, alkenyl, phenyl, aralkyl, aralkenyl, hydroxy, hydroxyalkyl, alkoxy, alkoxyalkyl, aralkoxy, acyloxy, halo, haloalkyl, nitro, amino, mono-and di-alkylamino, acylamino, carboxy, carboxyalkyl, carbalkoxy, carbaralkoxy, carbalkoxyalkyl, carbalkoxyalkenyl, aminoalkoxy, amido, mono- and di-alkylamido and N,N-cycloalkylamido, phenyl, or benzoyl; and R and R together may also form a ketone group.

Preferred X moieties are $(CHR_1)_{0-2}$, $CH_2$—Z—$CH_2$ or Z—$CH_2$, where Z is O, NR' or S;

A special embodiment of this invention includes those compounds where one of Ar I or Ar II is an azidophenyl moiety.

A further special embodiment of this invention includes those compounds where Ar II is cycloalkyl. Preferred group include cyclopentyl, cyclohexyl and cycloheptyl.

As employed above and throughout this disclosure, the following terms, unless otherwise indicated, shall be understood to have the following meanings:

"Monocyclic aryl" means a carbocyclic and/or heterocyclic aromatic ring. Preferred rings include phenyl, thienyl, pyridyl, 2(1H)-pyridonyl, 4(1H)-pyridonyl, furyl, pyrimidinyl, imidazolyl, thiazolyl, oxazolyl and tetrazolyl.

"Bicyclic aryl" means a bicyclic ring system composed of two fused carbocyclic and/or heterocyclic aromatic rings. Preferred rings include naphthyl, indolyl, benzothienyl, benzofuranyl, quinolinyl, chromonyl, 1 (2H)-isoquinolonyl, isoquinolinyl, benzimidazolyl, benzothiazolyl, quinoxalinyl, naphthyridinyl, cinnolinyl, phthalazinyl, pyrido[2,3-b] pyrazine, pyrido[3,4b]pyrazine, pyrido[3,2-c]pyridazine, pyrido[3,4-b]-pyridine, pteridine, and quinazolinyl.

"Alkyl" means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group. Preferred alkoxy groups include methoxy, ethoxy, propoxy and butoxy.

"Aryloxy" refers to an aryl-O-group. The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

The preferred acyloxy groups are acetoxy and benzyloxy;

"Halo" means halogen. Preferred halogens include chloride, bromide and fluoride.

The preferred haloalkyl group is trifluoromethyl.

The more preferred compounds of this invention include those compounds of Formula I where Ar I and Ar II are independently phenyl, naphthyl, 2(1H)-pyridonyl, pyridyl, quinolinyl, thienyl, 1 (2H)-isoquinolonyl, indolyl, napthyridenyl, pyrido[2,3-b]pyrazine, pyrido[3,4-b] pyrazine, pyrido [3,2-c]pyridazine, pyrido[3,4-b]-pyridine, pteridine, benzothiazolyl, quinoxalinyl, benzimidazolyl, quinolinyl-N-oxide, isoquinolinyl-N-oxide, quinazolinyl, quinoxalinyl-N-oxide, quinazolinyl-N-oxide, benzoxazinyl, phthalazinyl, or cinnolinyl; and R is hydrogen, alkyl, alkoxy, hydroxy, halo or trifluoromethyl.

More specifically the compounds described by this invention are shown by the following representative subgeneric formulae Ia–Iw:

Ia

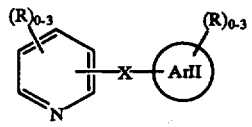

Ib

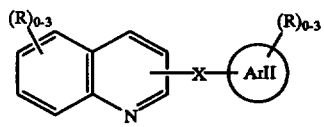

Ic

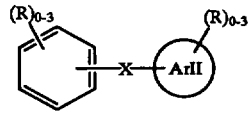

-continued

Id

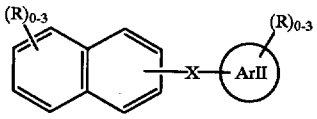

Ie

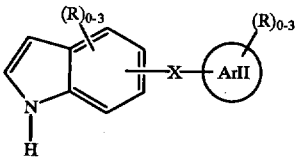

If

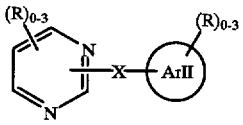

Ig

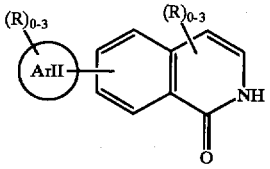

Ih

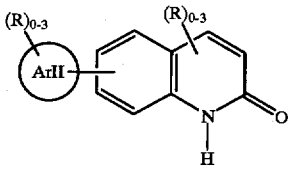

Ii

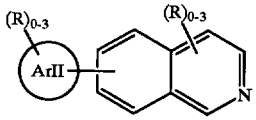

Ij

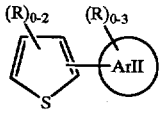

Ik

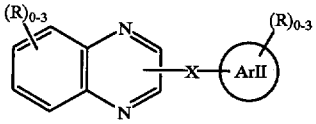

Im

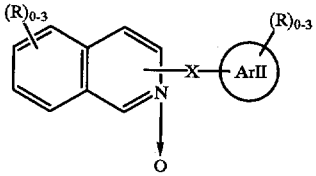

In

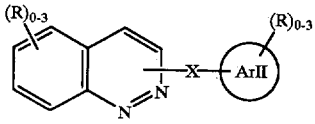

-continued

Io

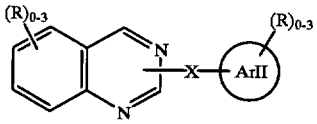

Ip

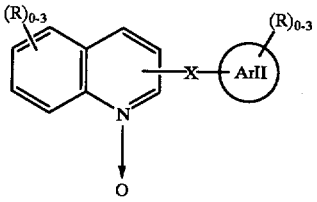

Iq

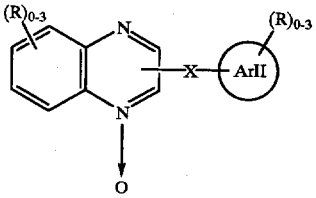

Ir

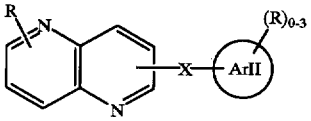

Is

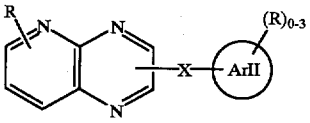

It

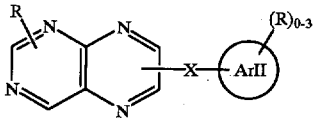

Iu

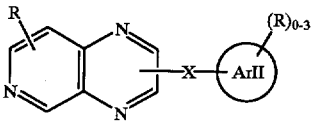

Iv

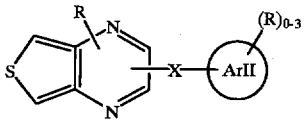

Iw

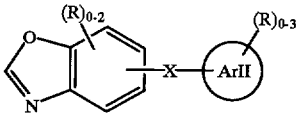

It should be understood that the R groups which are substituted in the above formulae Ia–Iw are located at any suitable and compatible position of each of the rings of the bicyclic system.

A special embodiment of this invention includes those compounds of the above formulae Ia–Iw where Ar II is thienyl, phenyl, naphthyl, pyridyl, quinolinyl, indolyl, furanyl, imidazolyl, 2(1H)-pyridonyl, 1 (2H)-isoquinolonyl, thiazolyl and cycloalkyl, Phenyl, thienyl naphthyl,or cycloalkyl are preferred.

A further special embodiment of this invention includes those compounds which are most preferred. These are described by the following formulae:

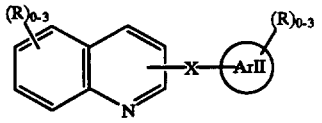

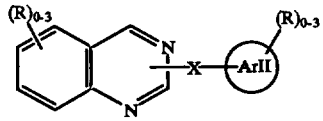

or

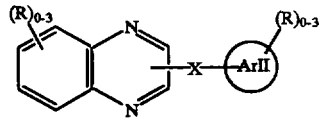

wherein

Ar II is phenyl, naphthyl, thienyl, cyclohexyl or cyclopentyl; and

X is a bond, methyl, ethyl, propyl or $(CHR_1)_m$—Z—$(CHR_1)_n$ where Z is O, NR', and n and m are 0–1 and n+m is 0 or 1.

The preferred classes of compounds include:

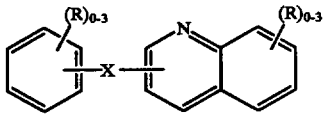

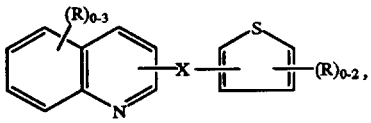

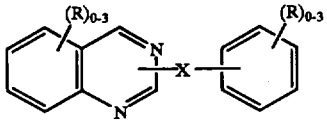

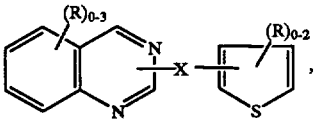

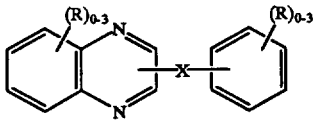

or

-continued

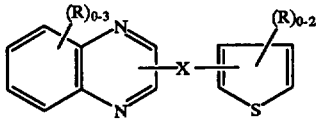

Compounds within the scope of this invention inhibit the growth factor induced autophosphorylation of PDGF and/or EGF receptors. It is believed that therapeutically useful PTK inhibiting compounds should not have appreciable activity as inhibitors of serine or threonine kinase systems. In addition these compounds should inhibit growth factor-induced cell proliferation. Compounds meeting these criteria are of considerable value and are particularly useful in the practice of the present invention. Compounds exhibiting selectivity for either of the above receptors are described herein.

The most preferred compounds are described where R is hydroxy, methoxy, ethoxy, chloro, bromo, fluoro or trifluoromethyl.

It is intended that the N-oxides of the above-described N-heteroaryl rings are encompassed within the scope of this invention.

The compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may be prepared by employing procedures known in the literature starting from known compounds or readily preparable intermediates. Exemplary general procedures follow.

In general the compounds useful for the method of inhibiting cell proliferation may be prepared by the coupling reaction of a palladium catalyzed aryl or heteroaryistannane with an aryl or heteroarylhalide or triflate.

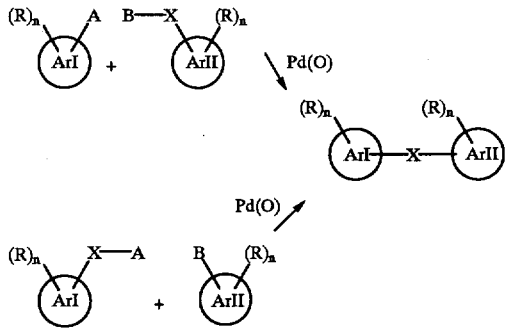

where X is halogen or triflate and Y is trialkylstannane and R and n are as previously described.

Preparation of aryl or heteroaryl substituted quinolines may be prepared as follows.

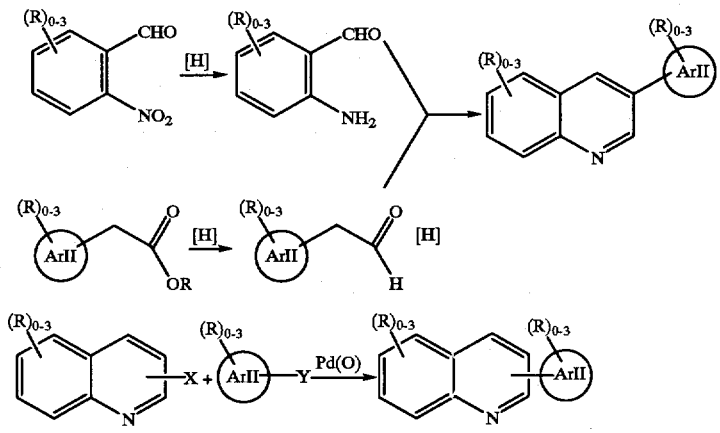

if X = halogen or triflate, then Y = trialkylstannane
if X = trialkylstannane, then Y = halogen or triflate The triflate may be prepared from the corresponding alcohol with triflic anhydride (trifluoromethanesulfonic anhydride) in pyridine

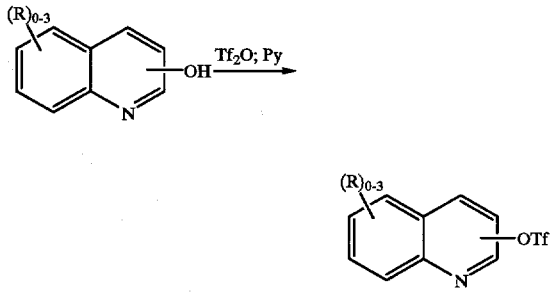

Other triflates suitable for coupling with the aryl and heteroarylstannanes may be prepared in a similar manner.

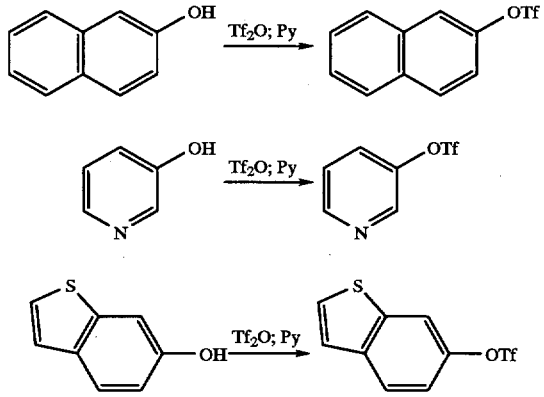

-continued

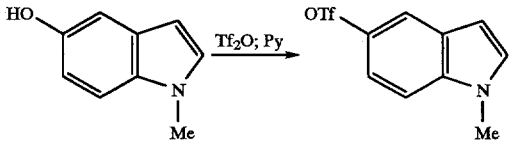

Triflates may also be prepared from 2(1 H) or 4(1 H) quinolones as shown by the following.

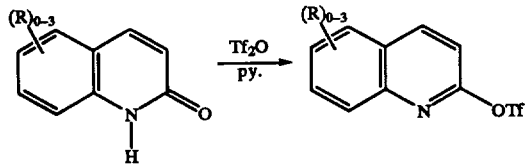

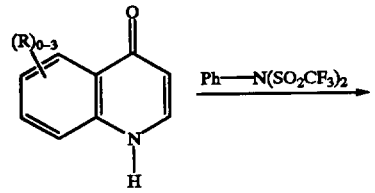

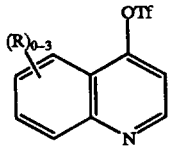

The triflimide such as used in the above reaction may also be used to prepare compounds having a particular substitution such as the following compound.

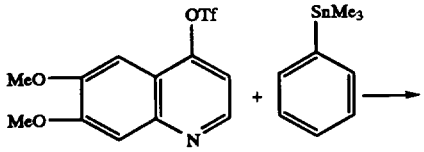

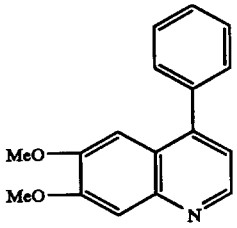

The aryl and heteroarylstannanes may be prepared from the corresponding halide (preferably bromide or iodide) by conversion to the aryllithium (by reaction with t-butyllithium at decreased temperatures, preferably about −78° C. followed by reaction with a halotrialkylstannane. The following reaction schemes give a representative list of stannanes prepared and the reaction conditions involved.

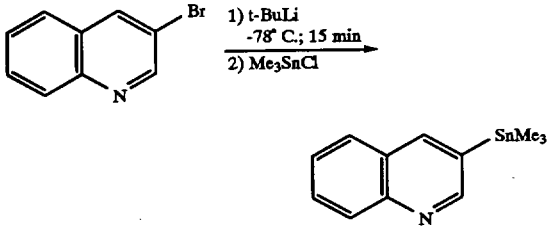

-continued

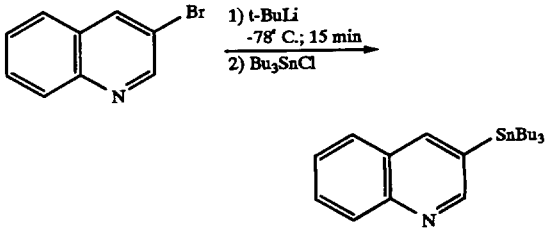

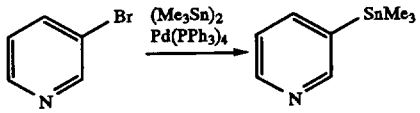

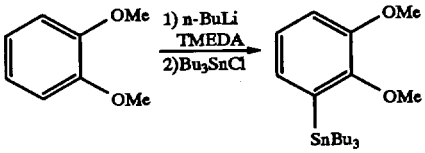

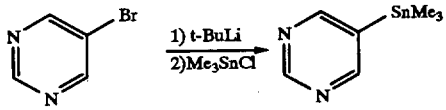

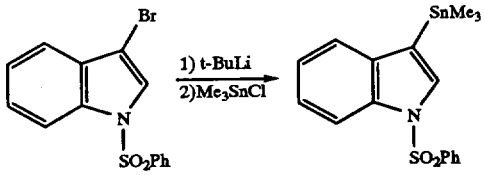

Further methods which may be employed in the preparation of stannanes of this invention include the following.

(1.) by the action of trimethyltin sodium on aryl halides as described in Chem. Pharm. Bull. 1982, 30, 1731–1737:

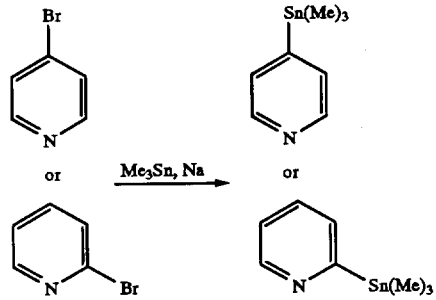

(2.) by heteroatom directed aromatic lithiation process:

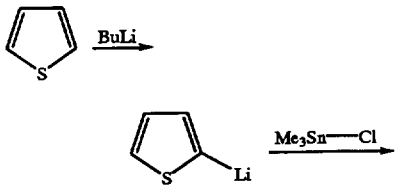

-continued
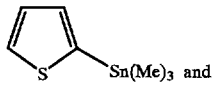
(3.) by halogen-lithium exchange:
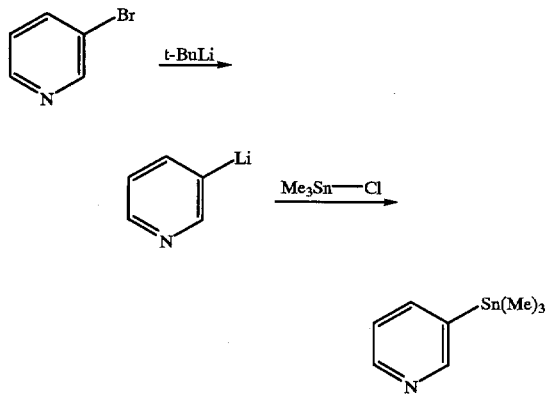
The following are representative coupling reactions which show the preparation of compounds used for the inhibition of cell proliferation
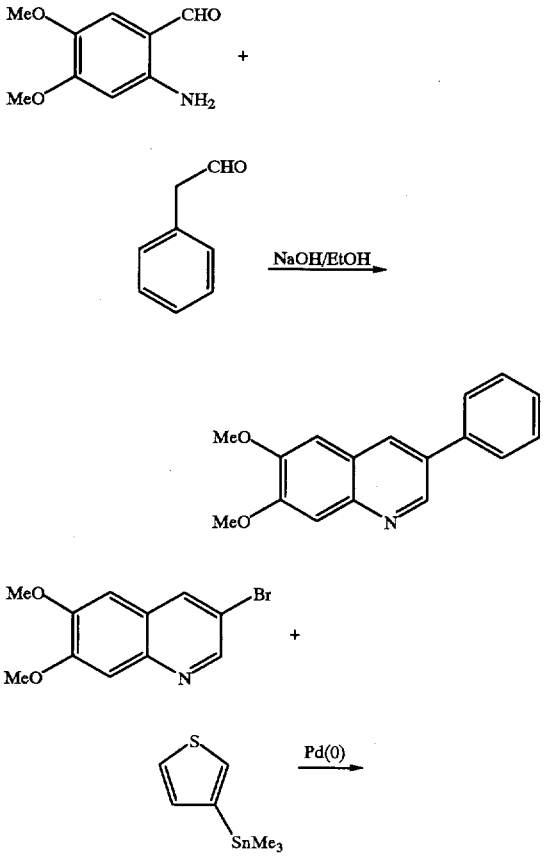
-continued
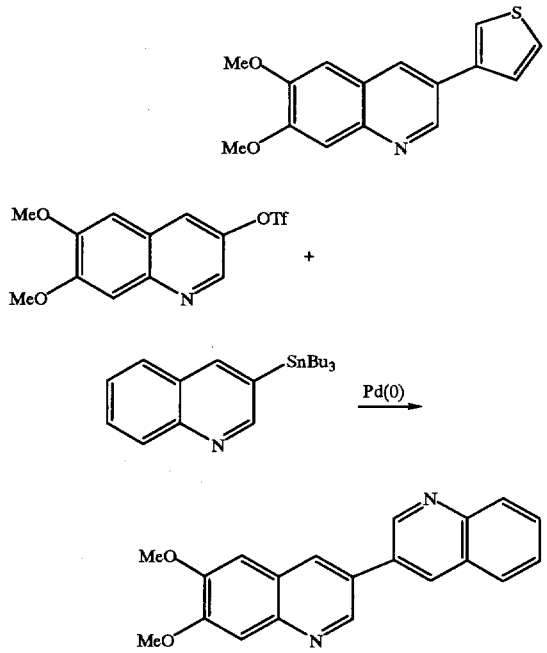
Of course various methods may be employed depending on the reactants involved. Thus, for example, in order to prepare
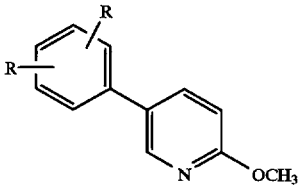
the following methods may be used:
Method A:
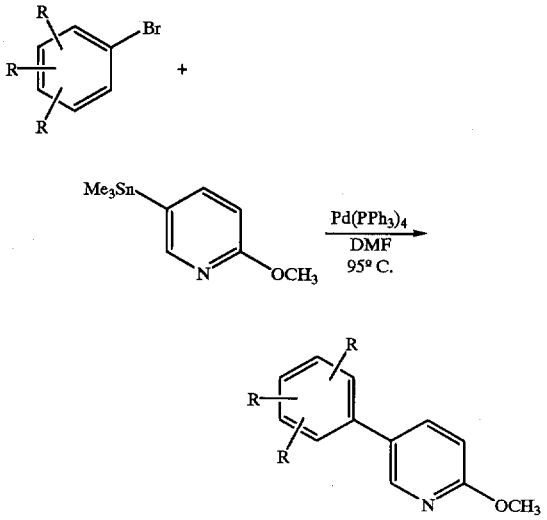

-continued

Method B:

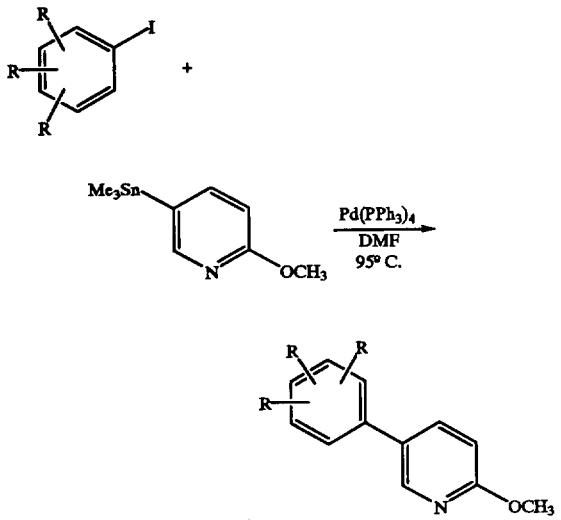

Method C:

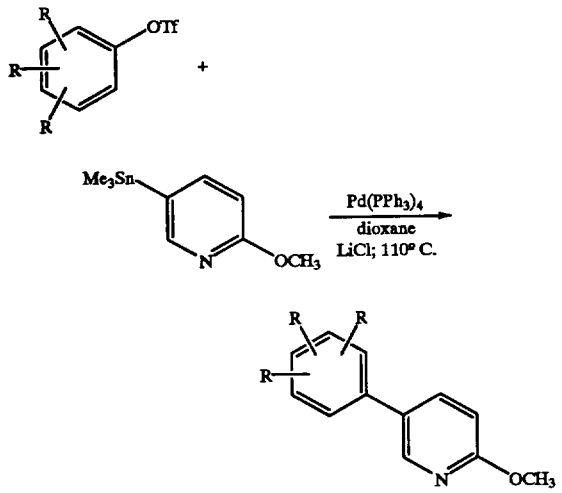

Method D:

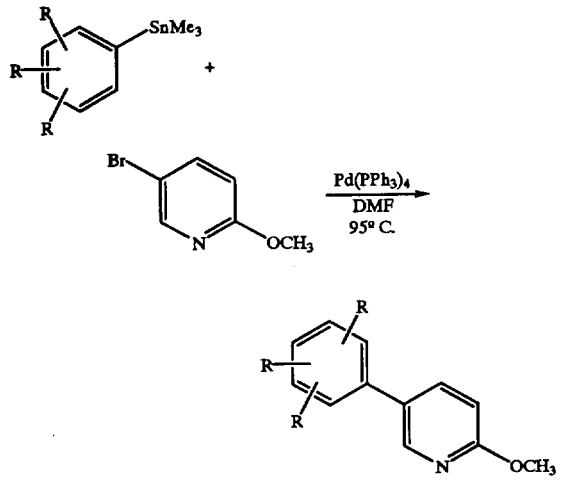

When it is desired that the final product include a 2-(1H) pyridone or 4-(1H) pyridone ring then it is convenient to carry out the condensation on the 2- or 4-alkoxy pyridine followed by selective dealkylation. This can be seen by the following representative scheme.

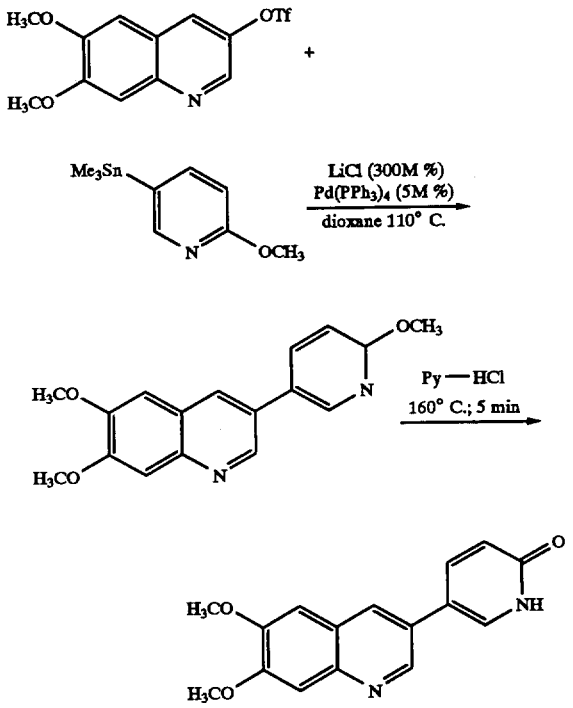

More specifically preparation of aryl or heteroaryl substituted 2(1H)-pyridones may be found in U.S. Pat. Nos. 3,715,358; 3,718,743; 4,465,686 and 4,599,423. Substituted phenyl pyridine preparation may be found in J. Am. Chem. Soc. 111, 877–891 (1989).

Thus it will be a matter of condensing two rings as shown above under the methods described and/or in the art in order to obtain the compounds useful in the practice of inhibition of cell proliferation of this invention. The following representative compounds are prepared as shown below:

5-(2,4,5-trihydroxyphenyl)-2(1H)-pyridone, 5-(1,4-dihydroxynaphth-2-yl)-2(1H)-pyridone, 5-(2,5-dihydroxyphenyl)-2(1H)-pyridone, 5-(2,5-dihydroxy-4-t-butylphenyl)-2(1H)-pyridone, 3-(2,5-dihydroxyphenyl)-4(1H)-pyridone, 3-(2,5-dihydroxy-4-t-butylphenyl)-4(1H)-pyridone, 3-(thien-3-yl)-6,7-dimethoxyquinoline, 3-(pyrid-3-yl)indole, 2-(2,5-dihydroxy-4t-butylphenyl)pyridine and 4-(2,5-dihydroxyphenyl)-1(2H)-isoquinolone.

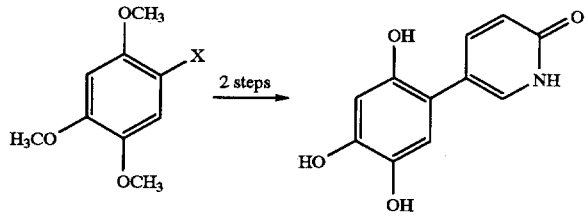
OCH3
X
2 steps
H3CO
OCH3
OH
O
NH
HO
OH
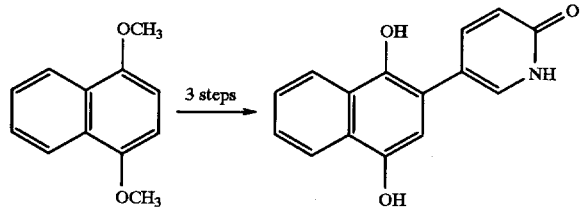
OCH3
3 steps
OCH3
OH
O
NH
OH
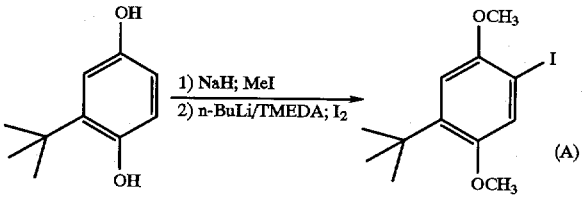
OH
1) NaH; MeI
2) n-BuLi/TMEDA; I2
OH
OCH3
I
OCH3
(A)
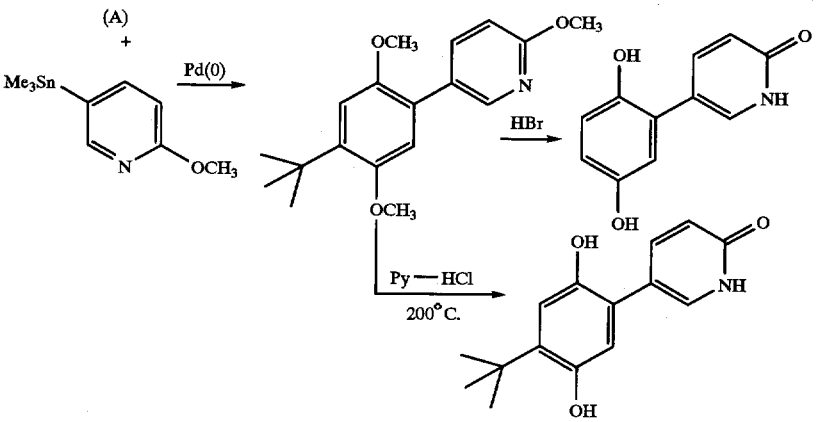
(A)
+
Me3Sn
N
OCH3
Pd(0)
OCH3
OCH3
N
HBr
OH
O
NH
OH
OCH3
Py—HCl
200° C.
OH
O
NH
OH
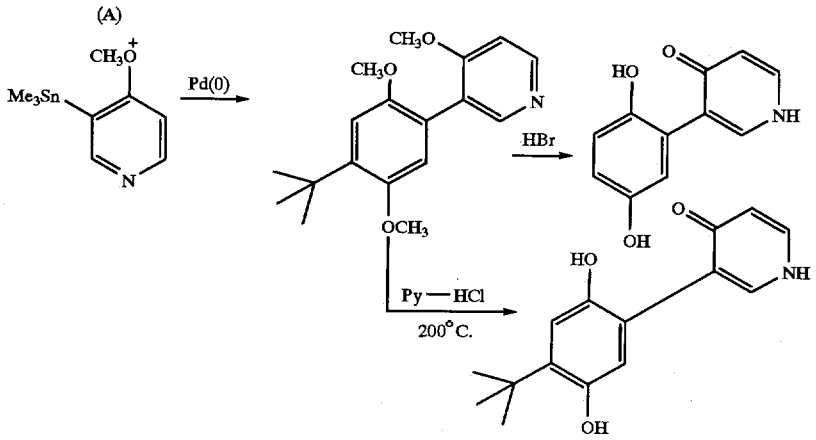
(A)
CH3O+
Me3Sn
N
Pd(0)
CH3O
CH3O
N
HBr
HO
O
NH
OH
OCH3
Py—HCl
200° C.
HO
O
NH
OH -continued

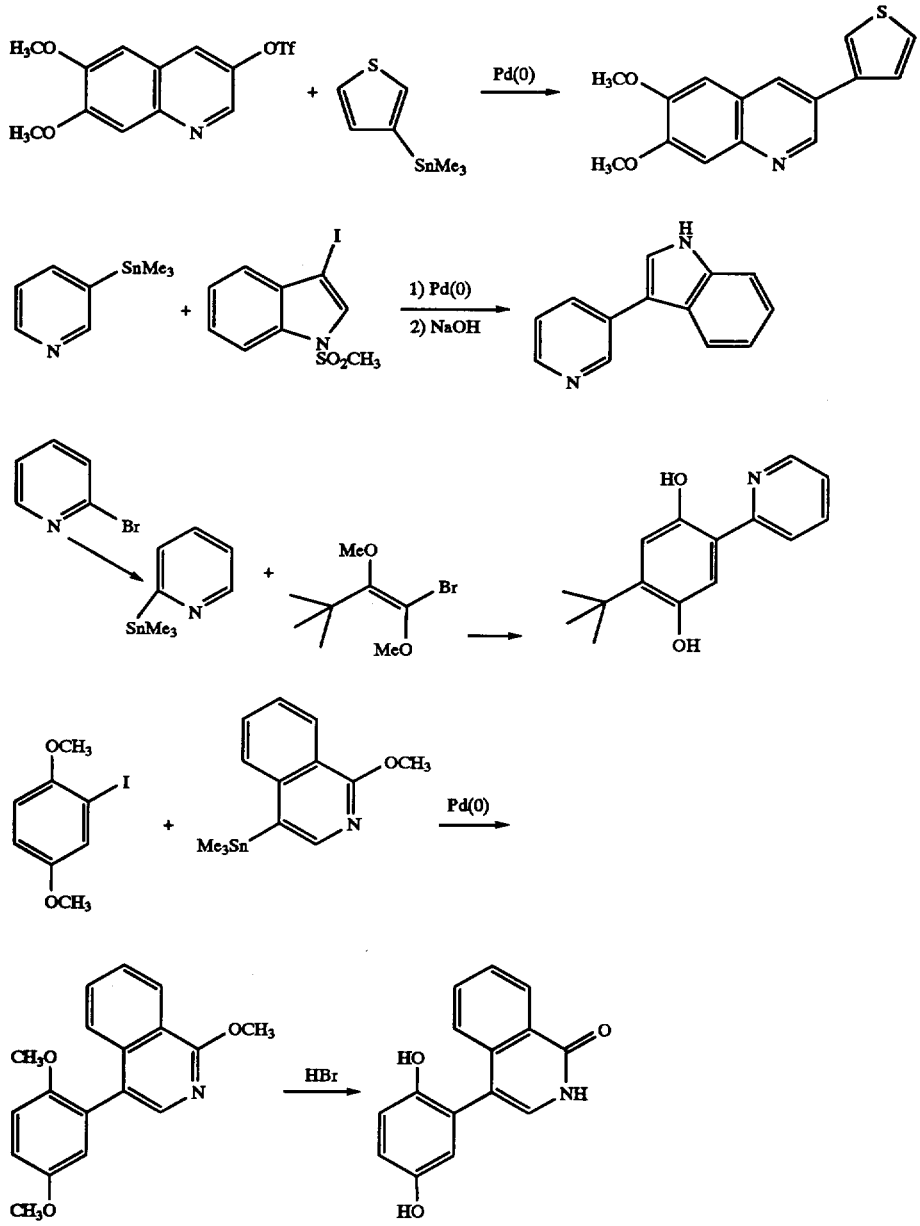

The compounds of the present invention may be prepared by the following representative examples.

EXAMPLE 1

2-methoxy-5-trimethylstannylpyridine

A solution of 1.74 g (9.26 mmol) of 2-methoxy-5-bromopyridine, 3.84 mL (6.07 g; 18.5 mmol) of hexamethylditin and 516 mg (0.446 mmol) of Pd (PPh3)4 in mL of dry toluene is flushed thoroughly with nitrogen and heated to 90° C. for 4 hours. The mixture is then evaporated and chromatographed on silica gel (eluting with hexane and then with 95:5 hexane/ethyl acetate) to give 2-methoxy-5-trimethylstannylpyridine as a colorless oil which is used directly in the next step.

EXAMPLE 2

When the procedure of Example 1 is followed and 2-methoxy-5-bromopyridine is replaced by the compounds of Table I below, then the compounds of Table II below are prepared. (Methods outlined on pages 14 and may also be used.)

TABLE I 2-methoxyphenyl bromide
3-methoxyphenyl bromide
4-methoxyphenyl bromide
2,3-dimethoxyphenyl bromide
2,4-dimethoxyphenyl bromide
2,5-dimethoxyphenyl bromide
2,6-dimethoxyphenyl bromide
3,4-dimethoxyphenyl bromide
3,5-dimethoxyphenyl bromide
3,4,5-trimethoxyphenyl bromide 2,3,4-trimethoxyphenyl bromide
2,5-dimethoxy-4-t-butylphenyl bromide
2,5-dimethoxy-4-phenylphenyl bromide
2,4dimethylphenyl bromide
2,5-dimethylphenyl bromide
2-methyl-5-methoxyphenyl bromide
4-chlorophenyl bromide
4-fluorophenyl bromide
2,5-dichlorophenyl bromide
3,4-dichlorophenyl bromide
4-dimethylaminophenyl bromide
4-acetylaminophenyl bromide
4-(N,N-dimethylaminocarbonyl)phenyl bromide
4-t-butoxycarbonylphenyl bromide
4-(pyrrolidinocarbonyl)phenyl bromide
3,5-bis(trifluoromethyl)phenyl bromide
4-bromobiphenyl
2-bromopyridine
3-bromopyridine
4-bromopyridine
2-methoxy-5-bromopyridine
4-methoxy-5-bromopyridine
6-methoxy-5-bromopyridine
2,3-dimethoxy-5-bromopyridine
2,4-dimethoxy-5-bromopyridine
2-acetylamino-5-bromopyridine
2-bromothiophene
3-bromothiophene
2-methoxy-3-bromothiophene
2-methoxy-4-bromothiophene
2-methoxy-5-bromothiophene
3-methoxy-5-bromothiophene
4-methoxy-2-bromothiophene
3-bromofuran
t-butyl 5-bromo-2-furoate
2-bromothiazole
2-bromooxazole
1-methyl-3-bromopyrazole
5-bromopyrimidine
2-bromopyrazine
4-bromopyridazine
'-bromonaphtbalene
2-bromonaphthalene
2-bromo-6-methoxynaphthalene
2-bromo-6,7-dimethoxynaphthalene
2-bromoquinoline
3-bromoquinoline
4-bromoquinoline
5-bromoquinoline
6-bromoquinoline
6,7-dimethoxy-3-bromoquinoline
6-methoxy-3-bromoquinoline
7-methoxy-3-bromoquinoline
7,8-dimethoxy-3-bromoquinoline
6,7-dichloro-3-bromoquinoline
4-bromoisoquinoline
3-bromoisoquinolihne
1-bromoisoquinoline
6,7-dimethoxy-3-bromoisoquinoline
N-methanesulfonyl-3-bromoindole
N-methanesulfonyl-5-brqmoindole
N-methanesulfonyl-3-bromo-5-methoxyindole
N-methanesulfonyl-3-bromo-5-chloroindole
2-bromobenzothiophene
3-bromobenzothiophene
8-bromopurine
7-methyl-2-bromopurine
3-bromopyrido-[3,4-b]-pyridine

TABLE II 2-methoxyphenyl trimethylstannane
3-methoxyphenyl trimethylstannane
4-methoxyphenyl trimethylstannane
2,3-dimethoxyphenyl trimethylstannane
2,4-dimethoxyphenyl trimethylstannane
2,5-dimethoxyphenyl trimethylstannane
2,6-dimethoxyphenyl trimethylstannane
3,4dimethoxyphenyl trimethylstannane
3,5-dimethoxyphenyl trimethylstannane
3,4,5-trimethoxyphenyl trimethylstannane
2,3,4-trimethoxyphenyl trimethylstannane
2,5-dimethoxy-4-t-butylphenyl trimethylstannane
2,5-dimethoxyphenylphenyl trimethylstannane
2,4-dimethylphenyl trimethylstannane
2,5-dimethylphenyl trimethylstannane
2-methyl-5-methoxyphenyl trimethylstannane
4-chlorophenyl trimethylstannane
4-fluorophenyl trimethylstannane
2,5-dichlorophenyl trimethylstannane
3,4-dichlorophenyl trimethylstannane
4-dimethylaminophenyl trimethylstannane
4-acetylaminophenyl trimethylstannane
4-(N,N-dimethylaminocarbonyl)phenyl trimethylstannane
4-t-butoxycarbonylphenyl trimethylstannane
4-(pyrrolidinocarbonyl)phenyl trimethylstannane
3,5-bis(trifluoromethyl)phenyl trimethylstannane
4-trimethylstannylbiphenyl
2-trimethylstannylpyridine
3-trimethylstannylpyridine
4-trimethylstannylpyridine
2-methoxy-5-trimethylstannylpyridine
4-methoxy-5-trimethylstannylpyridine
6-methoxy-5-trimethylstannylpyridine
2,3-dimethoxy-5-trimethylstannylpyridine
2,4-dimethoxy-5-trimethylstannylpyridine
2-acetylamino-5-trimethylstannylpyridine
2-trimethylstannylthiophene
3-trimethylstannylthiophene
2-methoxy-3-trimethylstannylthiophene
2-methoxy-4-trimethylstannylthiophene
2-methoxy-5-trimethylstannylthiophene
3-methoxy-5-trimethylstannylthiophene 4-methoxy-2-trimethylstannylthiophene
3-trimethylstannylfuran
t-butyl 5-trimethylstannyl-2-furoate
2-trimethylstannylthiazole
2-trimethylstannyloxazole
1-methyl-3-trimethylstannylpyrazole
5-trimethylstannylpyrmidine
2-trimethylstannylpyrazine
4-trimethylstannylpyridazine
1-trimethylstannylnaphthalene
2-trimethylstannylnaphthalene
2-trimethylstannyl-6-methoxynaphthalene
2-trimethylstannyl-6,7-dimethoxynaphthalene
2-trimethylstannylquinoline
3-trimethylstannylquinoline
4-trimethylstannylquinoline
5-trimethylstannylquinoline
6-trimethylstannylquinoline
6,7-dimethoxy-3-trimethylstannylquinoline
6-methoxy-3-trimethylstannylquinoline
7-methoxy-3-trimethylstannylquinoline
7,8-dimethoxy-3-trimethylstannylquinoline
6,7-dichloro-3-trimethylstannylquinoline
4-trimethylstannylisoquinoline
3-trimethylstannylisoquinoline
1-trimethylstannylisoquinoline
6,7-dimethoxy-3-trimethylstannylisoquinoline
N-methanesulfonyl-3-trimethylstannylindole
N-methanesulfonyl-5-trimethylstannylindole
N-methanesulfonyl-3-trimethylstannyl-5-methoxyindole
N-methanesulfonyl-3-trimethylstannyl-5-choroindole
2-trimethylstannylbenzothiophene
3-trimethylstannylbenzothiophene
8-trimethylstannylpurine
7-methyl-2-trimethylstannylpurine
3-trimethylstannylpyrido-[3,4-b]-pyridine

EXAMPLE 3

6,7-dimethoxyquinolin-3-yl trifluoromethanesulfonate,

A solution of 1.84 g (8.98 mmol) of 3-hydroxy-6,7-dimethoxyquinoline in mL of dry pyridine is cooled to 0° C. and 3.20 mL (5.38 g; 19.1 mmol) of trifluoromethanesulfonic anhydride is added via syringe. The solution is allowed to warm to 22° C. and stirred for 4 hours. The solution is then partitioned between ethyl acetate (150 mL) and water (100 mL). The aqueous layer is back extracted with ethyl acetate (100 mL) and the combined organics dried ($Na_2SO_4$) and evaporated. The resulting residue is chromatographed on silica gel (eluting with chloroform) to give a white solid which is recrystallized from hexane to give 6,7-dimethoxyquinolin- 3-yl trifluoromethane-sulfonate. mp 82.5°–85° C.)

EXAMPLE 4

When the procedure of Example 3 is followed and 3-hydroxy-6,7-dimethoxyquinoline is replaced by the compounds of Table III below, then the products of Table IV are prepared

TABLE III phenol
2-methoxyphenol
3-methoxyphenol
4-methoxyphenol
2,3-dimethoxyphenol
3,4-dimethoxyphenol
3,5-dimethoxyphenol
3,4,5-trimethoxyphenol
2-chlorophenol
3-chlorophenol
4-chlorophenol
4-bromophenol
2,4-dichlorophenol
2,5-dichlorophenol
3,5-dichlorophenol
3,5-bis(trifluoromethyl)phenol
3-dimethylaminophenol
o-cresol
m-cresol
p-cresol
α,α,α-trifluoro-p-cresol
3-ethylphenol
4-tert-butylphenol
2,4-dimethylphenol
2,5-dimethylphenol
3,4-dimethylphenol
4-benzyloxyphenol
4-phenylphenol
2-phenylphenol
2,3,5-trimethyphenol
4-nitrophenol
4-acetylaminophenol
2-bromo-4-methylphenol
3'-hydroxyacetophenone
4'-hydroxyacetophenone
methyl 3-hydroxybenzoate
methyl 4-hydroxy-3-methoxybenzoate
N,N-dimethyl-4-hydroxybenzamide
1-naphthol
2-naphthol
6-methoxy-1-naphthol
6-methoxy-2-naphthol
6,7-dimethoxy-1-naphthol
6,7-dimethoxy-2-naphthol
5,8-dimethoxy-2-naphthol
6-bromo-2-naphthol
2-hydroxyquinoline
2-hydroxy-4-methylquinoline
6,7-dimethoxy-2-hydroxyquinoline
3-hydroxyquinoline
4-hydroxyquinoline
6,7-dimethoxy-4-hydroxyquinoline
7-chloro-4-hydroxyquinoline
1-hydroxyisoquinoline
5-hydroxyisoquinoline
2-hydroxypyridine
3-hydroxypyridine
4-hydroxypyridine 2,3-dimethoxy-5-hydroxypyridine
5-chloro-2-pyridinol
5-chloro-3-pyridinol
3-hydroxypicolinamide

TABLE IV phenyl trifluoromethane sulfonate
2-methoxyphenyl trifluoromethane sulfonate
3-methoxyphenyl trifluoromethane sulfonate
4-methoxyphenyl trifluoromethane sulfonate
2,3-dimethoxyphenyl trifluoromethane sulfonate
3,4-dimethoxyphenyl trifluoromethane sulfonate
3,5-dimethoxyphenyl trifluoromethane sulfonate
3,4,5-trimethoxyphenyl trifluoromethane sulfonate
2-chlorophenyl trifluoromethane sulfonate
3-chlorophenyl trifluoromethane sulfonate
4-chlorophenyl trifluoromethane sulfonate
4-bromophenol trifluoromethane sulfonate
2,4-dichlorophenyl trifluoromethane sulfonate
2,5-dichlorophenyl trifluoromethane sulfonate
3,5-dichlorophenyl trifluoromethane sulfonate
3,5-bis(trifluoromethyl)phenyl trifluoromethane sulfonate
3-dimethylaminophenyl trifluoromethane sulfonate
o-cresyl trifluoromethane sulfonate
m-cresyl trifluoromethane sulfonate
p-cresyl trifluoromethane sulfonate
α,α,α-trifluoro-p-cresyl trifluoromethane sulfonate
3-ethylphenyl trifluoromethane sulfonate
4-tert-butylphenyl trifluoromethane sulfonate
2,4dimethylphenyl trifluoromethane sulfonate
2,5-dimethylphenyl trifluoromethane sulfonate
3,4-dimethylphenyl trifluoromethane sulfonate
4-benzyloxyphenyl trifluoromethane sulfonate
2-phenylphenyl trifluoromethane sulfonate
4-phenylphenyl trifluoromethane sulfonate
2,3,5-trimethyphenyl trifluoromethane sulfonate
4-nitrophenyl trifluoromethane sulfonate
4-acetamidophenyl trifluoromethane sulfonate
2-bromo-4-methylphenyl trifluoromethane sulfonate
3-acetylphenyl trifluoromethane sulfonate
4-acetylphenyl trifluoromethane sulfonate
3-methoxycarbonylphenyl trifluoromethane sulfonate
2-methoxy-4-methoxycarbonylphenyl trifluoromethane sulfonate
4-N,N-dimethylaminocarbonylphenyl trifluoromethane sulfonate
naphth-1-yl trifluoromethane sulfonate
naphth-2-yl trifluoromethane sulfonate
6-methoxynaphth-1-yl trifluoromethane sulfonate
6-methoxynaphth-2-yl trifluoromethane sulfonate
6,7-dimethoxynaphth-1-yl trifluoromethane sulfonate
6,7-dimethoxynaphth-2-yl trifluoromethane sulfonate
5,8-dimethoxynaphth-2-yl trifluoromethane sulfonate
6-bromonaphth-2-yl trifluoromethane sulfonate
quinolin-2-yl trifluoromethane sulfonate
4-methylquinolin-2-yl trifluoromethane sulfonate
6,7-dimethoxyquinolin-2-yl trifluoromethane sulfonate
quinolin-2-yl trifluoromethane sulfonate
quinolin-4-yl trifluoromethane sulfonate
6,7-dimethoxyquinolin-4-yl trifluoromethane sulfonate
7-chloroquinolin-4-yl trifluoromethane sulfonate
isoquinolin-1-yl trifluoromethane sulfonate
isoquinolin-5-yl trifluoromethane sulfonate
pyridin-2-yl trifluoromethane sulfonate
pyridin-3-yl trifluoromethane sulfonate
pyridin-4-yl trifluoromethane sulfonate
2,3-dimethoxypyridin-5-yl trifluoromethane sulfonate
5-chloro-2-pyridin-2-yl trifluoromethane sulfonate
5-chloro-3-pyridinyl trifluoromethane sulfonate
picolin-3-amido trifluoromethane sulfonate

EXAMPLE 5

2.5-dimethoxy-4-t-butylphenyl iodide

A stirred solution of 3.00 g (15.5 mmol) of 1,4-dimethoxy-2-t-butylbenzene (obtained by methylation of t-butyl hydroquinone with sodium hydride and methyl iodide in tetrahydrofuran) and 2.52 g (21.7 mmol) of tetramethylethylenediamine in 50 mL of anhydrous ether under nitrogen is cooled to 0° C. and 8.66 mL (21.7 mmol) of n-butyllithium (2.5M in hexane) is added over a 5 minute period. The mixture is warmed to 22° C., stirred for 18 hours and then cooled back to 0° C. The reaction is quenched with 7.86 g (30.9 mmol) of iodine in 30 mL of tetrahydrofuran and partitioned between ethyl acetate (200 mL) and 10% NaHSO3 (300 mL). The organic layer is washed with water (50 mL), brine (50 mL), dried (MgSO4) and evaporated to give a brown, partially crystalline oil which is chromatographed on silica gel (eluting with 98:2 hexane/ethyl acetate) to give crude product which is recrystallized from hexane to obtain 2,5-dimethoxy-4-t-butylphenyl iodide m p 8.5°–82.5° C.)

EXAMPLE 6

When the procedure of Example 5 is followed and the appropriate starting material is used, the following compounds of Table V may be prepared.

TABLE V 2,3-dimethoxyphenyl iodide
2,3,4-trimethoxyphenyl iodide
2,4-dimethoxy-3-t-butylphenyl iodide
4-iodo-1,3-benzodioxole

EXAMPLE 7

5-(3,4-dimethoxyphenyl)-2-methoxypyridine

A solution of 2.00 g (6.64 mmol) of 4-trimethylstannylveratrole, 2.49 g (13.2 mmol) of 2-methoxy-5-bromopyridine and 370 mg (0.332 mmol) of Pd $(PPh_3)_4$ in 30 mL of dry dimethylformamide is flushed thoroughly with nitrogen and heated to 90° C. for 12 hours. The reaction mixture is partitioned between ethyl acetate (150 mL) and water (100 mL). The aqueous layer is back extracted with ethyl acetate (100 mL) and the combined organics are washed with brine (75 mL), dried ($MgSO_4$) and evaporated to give a crude yellow oil. The oil is chromatographed on silica gel (eluting with 95:5 hexane/ethyl acetate and then with 9:1 hexane/ethyl acetate) which gives 5-(3,4-dimethoxy-phenyl)-2-methoxypyridine m.p 83°–84° C.)

EXAMPLE 8

When the procedure of Example 7 is followed and 2-methoxy-5-bromopyridine is replaced with the bromo compounds of Example 2, Table I, then the corresponding products are obtained.

EXAMPLE 9

When the procedure of Example 7 is followed and 4-trimethylstannylveratrole is replaced by the stannanes of Example 2, Table II, then the corresponding products are obtained.

EXAMPLE 10

When the procedure of Example 7 is followed and 2-methoxy-5-bromopyridine is replaced with the bromo compounds of Example 2, Table I and 4-trimethylstannylveratrole is replaced by the stannanes of Example 2, Table II, then the corresponding products are obtained. A representative list of compounds so prepared are shown below In Table VI.

TABLE VI 2-(2,3,4-trimethoxyphenyl)pyridine
2,3-dimethoxy-6-(thien-3-yl)naphthaylene
3-(2,3-dimethoxypbenyl)quinoline
3-(benzothien-3-yl)quinoline
4-(phenyl)phenyl-1,4-dimethoxybenzene
2-(2,5-dimethoxyphenyl)naphthaylene
5-(2,5-dimethoxyphenyl)pyrimidine
5-phenyl-1,2,4-trimethoxybenzene
2-methoxy-5-(2,3,5-trimethoxyphenyl)pyridine
2-methoxy-5-(1,4-dimethoxynaphth-2-yl)pyridine
3-(2,5-dimethoxyphenyl)thiophene
2-methoxy-5-(2,5-dimethoxy-4-phenyl)phenylpyridine
3,6-dihydroxy-4-phenylveratrole
4-(2,5-dimethoxyphenyl)veratrole

EXAMPLE 11

3-(2-methoxypyridin-5,yl)-6,7-dimethoxyquinoline

A mixture of 800 mg (2.94 mmol) of 2-methoxy-5-trimethylstannyl-pyridine, mg (2.94 mmol) of 6,7-dimethoxyquinolin-3-yl trifluoromethane sulfonate, 374 mg (8.82 mmol) of anhydrous lithium chloride and 170 mg (0.147 mmol) of $Pd(PPh_3)hd$ in 15 mL of anhydrous dioxane is flushed thoroughly with nitrogen and refluxed for 6 hours. The mixture is diluted with ethyl acetate (100 mL), washed with saturated $NaHCO_3$ (75 mL), dried ($Na_2SO_4$) and evaporated. The resulting residue is chromatographed on silica gel (eluting with chloroform) to give a solid material which is recrystallized from ethyl acetate to give 3-(2-methoxypyrid-5-yl)-6,7-dimethoxyquinoline m.p. 170.5°–171.5° C.

EXAMPLE 12

When the procedure of Example 11 is followed and 2-methoxy-5-trimethylstannylpyridine is replaced by the stannanes of Example 2, Table II, then the corresponding products are obtained.

EXAMPLE 13

When the procedure of Example 11 is followed and 6,7-dimethoxy-quinolin-3-yl trifluoromethane sulfonate is replaced by the triflates of Example 4, Table IV, then the corresponding products are prepared.

EXAMPLE 14

When the procedure of Example 11 is followed and 2-methoxy-5-trimethylstannylpyridine is replaced by the stannanes of Example 2, Table II, and 6,7-dimethoxyquinolin-3-yl trifluoromethane sulfonate is replaced by the triflates of Example 4, Table IV, then the corresponding products are prepared. A representative list of compounds so prepared is shown below in Table VII.

TABLE VII 3-(thien-3-yl)-6,7-dimethoxyquinoline, mp. 116°–118° C.
2-methoxy-5-(3,4,5-trimethoxyphenyl)pyridine, m.p. 71°–72° C.
4-(thien-3-yl)-6,7-dimethoxyquinoline, m.p. 134°–135° C.
2-(thien-3-yl)-6,7-dimethoxyquinoline, 135.5°–138° C.
3-(quinolin-3-yl)-6,7-dimethoxyquinoline, m.p. 190.5°–191° C.
3-(thien-3-yl)-6,7-dichloroquinoline, m.p. 167°–167.5° C.
3-(thien-3-yl)-7-methoxyquinoline, m.p. 122°–124° C.
3-(3,4-dichlorophenyl)-6,7-dimethoxyquinoline, m.p. 184°–186° C.
3-(4-methoxyphenyl)-6,7-dimethoxyquinoline, m.p. 162.5°–164.5° C.
3-(naphth-2-yl)-6,7-dimethoxyquinoline, m.p. 162.50°–165° C.
3-(4-phenyl)phenyl-6,7-dimethoxyquinoline, m.p. 143°–145° C.
3-(thien-2-yl)-6,7-dimethoxyquinoline, m.p. 122.5°–124° C.
3-(5-methoxythien-2-yl)-6,7-dimethoxyquinoline (111°–113° C.
4-phenyl-6,7-dimethoxyquinoline, m.p. 124°–125° C.
3-(5-chlorothien-2-yl)-6,7-dimethoxyquinoline (131.5°–132° C.
3-(furan-3-yl)quinoline, m.p. 87°–90° C.
5-(2,5-dimethoxyphenyl)pyridine, m.p. 92.5°–94.5° C.
5-(2,5-dimethoxyphenyl)-2-methoxypyridine (oil)

EXAMPLE 15

2.methoxy-5-[(2,5-dimethoxy-4-t-butyl)phenyl]pyridine

When the procedure of Example 7 is followed and 4-trimethylstannylveratrole is replaced with 2-methoxy-5-trimethylstannylpyridine and 2-methoxy-5-bromopyridine is replaced with 2,5-dimethoxy-4-t-butylphenyl iodide from Example 5, then the compound prepared is 2-methoxy-5-[(2,5-dimethoxy-4-t-butyl)phenyl] pyridine as an oil.

EXAMPLE 16

5[(2,5-dimethoxy-4-t-butyl)phenyl]pyridine

When 2-methoxy-5-trimethylstannylpyridine in Example 15 is replaced by 5-trimethylstannylpyridine, the compound prepared is 5-[(2,5-dimethoxy-4-t-butyl)phenyl] pyridine m.p. 92.5°–94.5° C.

EXAMPLE 17

5-[(2,5-dihydroxy-4t-butyl)phenyl]-2(1H)-pyridone

A mixture of 252 mg (0.837 mmol) of 2-methoxy-5-[(2,5-dimethoxy-4-t-butyl)-phenyl] pyridine and 7.0 g of pyridine hydrochloride is heated to 210° C. for 1 hour, cooled and diluted with 60 mL of water. The mixture is cooled lo 0° C., filtered, and recrystallized from methanol to obtain 5-[(2,5-dihydroxy4-t-butyl)-phenyl]-2(1H)-pyridone [m.p. 270°–5° C.(softens)>300° C.(dec)].

EXAMPLE 18

5-[(2,5-dihydroxy-4-t-butyl)phenyl)pyridine

When the procedure of Example 17 is followed and 2-methoxy-5-[(2,5-dimethoxy-4-t-butyl)phenyl]pyridine is replaced by 5-[2,5-dimethoxy-4-t-butyl)phenyl] pyridine, the product obtained is 5-[(2,5-dihydroxy-4-t-butyl)phenyl] pyridine m.p. 202°–204° C.

EXAMPLE 19

5-(2,5-dihydroxyphenyl)-2(1H)-pyridone

A solution of 502 mg (2.05 mmol) of 2-methoxy-5-(2,5-dimethoxyphenyl)pyridine in 20 mL of 48% hydrobromic acid (aqueous) is refluxed for 6 hours, cooled to ca. 25° C. and diluted with 150 mL of water. The mixture is neutralized with solid $NaHCO_3$, cooled to 0° C. and the resulting solid product collected by filtration. The solid is washed well with water, collected by centrifugation, then further purified by recrystalization in methanol to obtain 5-(2,5-dihydroxyphenyl)-2(1H)-pyridone m.p. 303°–306° C. dec).

EXAMPLE 20

When the procedure of Example 19 is followed and 2-methoxy-5-(2,5dimethoxyphenyl)pyridine is replaced by 2-methoxy-5-(3,4-dimethoxyphenyl)pyridine, 2-methoxy-5-(3,4,5-trimethoxyphenyl)pyridine or 5-(2,5-dimethoxyphenyl)pyridine, then the compounds prepared are 5-(3,4-dihydroxy-phenyl)-2(1H)-pyridone m.p. 307°–310° C.); 5-(3,4,5-trihydroxyphenyl)-2(1H)-pyridone m.p. 300° C.) and 5-(2,5-dihydroxyphenyl)pyridine m.p. 216°–218° C.).

EXAMPLE 21

When the procedure of Example 17 is followed and 2-methoxy-5-[(2,5-dimethoxy-4-t-butyl)phenyl]pyridine is replaced by 2-methoxy-5-(6,7-dimethoxy-quinolin-3-yl) pyridine and the reaction is carried out at 160° C. for 5 minutes, then the product prepared is 5-(6,7-dimethoxyquinolin-3-yl)-2(1H)-pyridone m.p. 259°–261° C.).

EXAMPLE 22

3-(6.7-dimethoxyquinolin-3-yl)pyridine

A solution of 600 mg (3.37 mmol) of methyl N-2-(pyrid-3-yl)vinylcarbamate in 10 mL of 6N $H_2SO_4$ is refluxed for 10 minutes, cooled to 0° C. and basified to pH 11 with 50% NaOH. A solution of 400 mg (2.03 mmol) of 2-amino-4,5-dimethoxybenzaldehyde is immediately added and the mixture refluxed for 2.5 hours, cooled to 22° C. and partitioned between ether (150 mL) and water (100 mL). The aqueous layer is back extracted with chloroform and the combined organics are dried ($MgSO_4$) and evaporated to obtain an oil which is recrystallized from hexane/ethyl acetate twice to give 3-(6,7-dimethoxyquinolin-3-yl)pyridine m.p. 131°–132° C.).

EXAMPLE 23

3-(indol-3-yl)-6.7-dimethoxyquinoline

A solution of 800 mg (5.03 mmol) of indol-3-ylacetaldehyde (obtained from diisobutylaluminum hydride reduction of the ester and used immediately) and 800 mg (4.42 mmol) of 2-amino-4,5-dimethoxybenzaldehyde in 15 mL of ethanol is flushed thoroughly with nitrogen, treated with 0.5 mL of 1M NaOH and heated to 80° C. for 3 hours. The mixture is cooled to 22° C. and partitioned between chloroform (150 ml) and brine (100 mL). The organic layer is dried ($MgSO_4$) and evaporated and the dark brown residue that results is chromatographed on silica gel (eluting with 97.5:2.5 chloroform/methanol). The product obtained is further chromatographed on silica gel (eluting with 98:2 ethyl acetate/methanol) and the resulting product is recrystallized from ethyl acetate to give 3-(indol-3-yl)-6,7-dimethoxyquinoline m.p. 204°–206° C.).

EXAMPLE 24

When the procedure of Example 23 is followed and 2-amino-4,5-dimethoxybenzaldehyde is replaced with 2-aminobenzaldehyde, then the product prepared is 3-(indol-3-yl)quinoline m.p. 173°–175° C.).

EXAMPLE 25

When the procedure of Example 23 is followed and indol-3-yl-acetaldehyde is replaced by phenylacetaldehyde then the product prepared is 3-phenyl-6,7-dimethoxyquinoline m.p. 126.5°–128° C.)

EXAMPLE 26

6,7-dimethoxy-4-hydroxy-3-(thien-3-yl)-2(1H)-quinoline

A mixture of (0.632g) 3,4-dimethoxyaniline, (1.00 g) diethyl thien-3-ylmalonate and (20 ml) diphenyl ether are heated at approximately 200° C. for 4 hours. The reaction mixture is extracted with 0. IN NaOH solution and the alkaline solution then acidified with IN HCl and cooled in an ice water bath. The precipitate is collected, washed with ether and dried. The solid is then heated in EtOH, filtered and the filtrate evaporated in vacuo to give a light brown solid which is triturated with ether, filtered, and dried to give 6,7-dimethoxy-4-hydroxy-3-(thien-3-yl)-2(1H)quinoline m.p. 300° C. dec.).

EXAMPLE 27

2-(thien-2-yl)-4-carboxy-6,7-dimethoxyquinoline

To a boiling solution of 2-thiophenecarboxaldehyde (1.22 ml), pyruvic acid (0.904 ml) and 50 ml absolute EtOH is added dropwise a solution of 3,4-dimethoxyaniline (2.00 g) in 100 ml EtOH. The mixture is refluxed for approximately 4 hours, then stored at room temperature overnight. The greenish-yellow precipitate is collected by filtration, washed with fresh EtOH then with ether and allowed to air dry to obtain 2-(thien-2-yl) carboxy-6,7-dimethoxyquinoline m.p. 260°–263° C.).

EXAMPLE 28

When the procedure of Example 26 is followed and 2-thiophenecarboxaldehyde is replaced with 3-pyridinecarboxaldehyde or 2-midazolcarboxaldehyde, then the products prepared are 2-(pyrid-3-yl)-4-carboxy-6,7-dimethoxyquinoline m.p. 275° C. dec) and 2-(imidazol-2-yl)-4-carboxy-6,7-dimethoxyquinoline m.p. 300° C. dec).

EXAMPLE 29

2-(N-phenylsulfonylindol-3-yl)-4-carboxy-6,7-dimethoxyquinoline

Pyruvic acid (0.486 ml) is added to a suspension of (2.00 g) of N-phenyl-sulfonyl-3-indolecarboxaldehyde in 100 ml absolute EtOH. The mixture is heated to reflux and a solution of 3,4dimethoxyaniline (1.074 g) in 50 ml absolute EtOH is added dropwise. The reaction is then refluxed for approximately three hours and stirred at RT for 72 hours. The yellow precipitate is collected by filtration, washed with EtOH then with ether and the solid collected. This is triturated with EtOAC/EtOH and dried and used directly in the next step.

EXAMPLE 30

2-(indol-3-yl)-4-carboxy-6,7-dimethoxyquinoline

A stirred solution of (0.547 g) of 2-(N-phenylsulfonylindol-3-yl)-4-carboxy-6,7-dimethoxyquinoline, $K_2CO_3$ (0.380 g), MeOH (40 ml) and $H_2O$ (10 ml) are heated to reflux. The MeOH is evaporated in vacuo, and the aqueous residue diluted with more $H_2O$, and acidified with 0.IN HCl to pH between 6°–7 while contained in an ice-bath. An orange solid precipitates. This is collected, washed with ether then dried under vacuum (0.1 mm at 22° C.) for a few hours to obtain 2-(indol-3-yl)-4-carboxy-6,7-dimethoxyquinoline m.p. 286° C. dec).

EXAMPLE 31

3-cyclohexylethyl-6,7-dimethoxyquinoline

Step A 3-cyclohexylethynyl-6,7-dimethoxyquinoline

This reaction is carried out under anhydrous conditions. Cyclohexylacetylene (700 mg; 6.47 mmol) in 10 mL. THF is cooled to 0° C. To this is added 2.5M n-BuLi (3.0 mL; 7.44 mmol) and stirred for 30 min. at 0° C. under $N_2$ atm and then 1.0M $ZnCl_2$ (7.4 mL; 7.44 mmol). This is allowed to warm to room temperature and stirred for ¾ hour. The reaction mixture is transferred via cannula to a flask containing 6,7-dimethoxyquinolin-3-yl trifluoromethane sulfonate (500 mg; 1.48 mmol) and $Pd(PPh_3)4$ (83 mg; 0.074 mmol) in 4 mL of THF. This is then heated to 50° C. under $N_2$ for 4½ hours. The reaction mixture is then poured into 90 mL of 10% $NH_4OH$, diluted with $CHCl_3$ and stirred for 20 min. The aqueous layer is separated, and the organic layer washed with brine, dried over $MgSO_4$, filtered, evaporated and chromatographed with 4:1 hexane: EtOAc to obtain 3-cyclohexylethynyl-6,7-dimethoxyquinoline, which is recrystallized from hexane, identified by NMR and used directly in the next step.

Step B 3-cyclohexylethyl-6,7-dimethoxyquinoline

To 3-cyclohexylethynyl-6,7-dimethoxyquinoline (215 mg; 0.73 mmol) in 10mL $CH_3OH$ and 20 mL glacial acetic acid is added 22 mg 10% Pd/C. $H_2$ is bubbled through the reaction mixture and then filtered, evaporated to dryness and diluted with distilled water. This is then neutralized with $Na_2CO_3$, extracted with EtOAc, washed with brine, dried ($MgSO_4$), evaporated to dryness and chromatographed with 8:2/hexane: EtOAc to obtain 3-cyclohexyl-ethyl-6,7-dimethoxyquinoline.

Calc'd: C: 76.22; H: 8.47; N: 4.69

Found: C: 75.08; H: 8.32; N: 4.59

EXAMPLE 32

3-benzyloxy-6,7-dimethoxyquinoline

To 3-hydroxy-6,7-dimethoxyquinoline (150 mg; 0.73 mmol) in 3 mL THF is added benzyl bromide (0.13 mL; 188 mg; 1.10 mmol) and Nail (59 mg; 1.46 mmol). This is stirred at room temperature for 1 hour and 25 mg of NaH added followed by 1,3-dimethyl-3,4,5,6-tetrahydro-2(1H) pyrimidinone (DMPU)(255 mg; 2.07 mmol) and stirred at room temperature for 3½ hours. The reaction mixture is partitioned between EtOAc and distilled $H_2O$ and extracted 2× with EtOAc. The latter is washed with brine, dried ($MgSO_4$), filtered, evaporated to dryness and chromatographed with 1% MeOH/$CHCl_3$ to obtain 3-benzyloxy-6,7-dimethoxyquinoline m.p. 146.5°–148.5° C.).

EXAMPLE 33

2,(thien-3-yl)-6,7-dimethylquinoxaline

Step A 3-thienylglyoxaldehyde hydrate

A mixture of selenium dioxide (5.276 g; 0.048 mol) in dioxane: water; 95:5 is heated to solution. To this is added 3-acetylthiophene (4.00 g; 0.032 mol) and the mixture refluxed for 5 hours. The precipitated selenium is filtered off and the filtrate concentrated in vacuo to give a yellow oil which is purified by FPLC using 20%: 30%; EtoAc: hexane to obtain a yellow solid which is then recrystalized from water to obtain 3-thienylglyoxaldehyde hydrate, which is used directly in the next step.

Step B 2-(thien-3-yl)-6,7-dimethylquinoxaline

To a cooled stirring solution of 4,5-diamino-o-xylene (1.00g; 6.3 mmol) in 20 ml. absolute ethanol is slowly added a solution of 3-thienylglyoxaldehyde hydrate (0.662 g; 4.9 mmol) in 20 ml. absolute ethanol. The mixture is refluxed for 1.5 hours, cooled in an ice bath, filtered and the collected material is washed with hexane and dried in vacuo to obtain 2-(thien-3-yl)-6,7-dimethylquinoxaline m.p. 142°–143.5° C.).

EXAMPLE 34

When the procedure of example 33 is followed, and 3-thienylglyoxaldehyde of Step B is replaced by the compounds of Table VIII, below and 4,5-diamino-σ-xylene of Step B is replaced by the compounds of Table IX, below, then the corresponding products are obtained.

Table VIII 3-thienylglyoxaldehyde
glyoxal
phenylglyoxal
4-methoxy-α-oxobenzeneacetaldehyde
3-fluoro-4-methoxy-α-oxobenzeneacetaldehyde
α-oxo-γ-phenylbutyraldehyde
α-oxo-4-pyridineacetaldehyde
α-oxo-3-pyridineacetaldehyde
α-oxo-2-pyridineacetaldehyde
3,4-dimethoxy-α-oxobenzeneacetaldehyde
α-oxo-2-thiopheneacetaldehyde
α-oxo-3-thiopheneacetaldehyde
5-chloro-α-oxo-2-thiopheneacetaldehyde
5-fluoro-α-oxo-2-thiopheneacetaldehyde
2,3-butanedione
pyravic aldehyde
5-(4-chlorophenyl)-α-oxo-2-thiopheneacetaldehyde
5-(5-chloro-2-thienyl)-α-oxo-2-thiopheneacetaldehyde
4-cyano-α-oxobenzeneacetaldehyde
4-(1H-tetrazol-5-yl)-α-oxobenzeneacetaldehyde
5-bromo-α-oxo-2-thiophenacetaldehyde

TABLE IX 4,5-diamino-σ-xylene
1,2-diaminobenzene
4,5-dimethyl-1,2-diaminobenzene
4,5-dimethoxy-1,2-diaminobenzene
3,5-dimethyl-1,2-diaminobenzene
3,5-dimethoxy-1,2-diaminobenzene
2,3-diaminopyridine
3,4-diaminopyridine
3,4-diaminotoluene
4,5-diaminopyrimidine
4,5-diethyl-1,2-diaminobenzene
4,5-diethoxy-1,2-diaminobenzene 3,4-diaminobenzotrifluoride 4-tert-butyl-1,2-diaminobenzene 4-(4-pyridyl)-1,2-diaminobenzene 4-(3-pyridyl)-1,2-diaminobenzene 5-bromo-2,3-diaminopyridine 5-bromo-3,4-diaminopyridine 4-fluoro-1,2-diaminobenzene 2-bromo-4,5 -diamopyridine 3,4-diaminothiophene 1,2-diaminocyclohexane

EXAMPLE 35

3-phenoxy-6,7-dimethylquinoline

To a solution of Nail (1.2g; 60% disp in oil) in DMF (3 ml) is added 3-hydroxy-6.7-dimethoxyquinoline (150 mg; 0.73 tool) and the reaction mixture is allowed to stir for 30 minutes at room temperature. To this is added the tetrafluoroborate salt of chlorobenzene manganese tricarbonyl complex (prepared by J.O.C. 24: 1991;7092) (183 mg) and stirred for 3 hours. To this is added 20 ml of acetonitrile and stirred overnight. The reaction mixture is dissolved in EtOAc: brine and extracted 2x with EtOAc, washed with water 2x, washed with brine, dried ($MgSO_4$) and concentrated in vacuo to obtain a material which is purified by FPLC using 1% methanol: chloroform to obtain a solid which NMR indicates to be 3-phenoxy-6.7-dimethoxyquinoline. The hydrochloride salt is then prepared in the usual manner m.p. 224–226).

EXAMPLE 36

(6,7-dimethoxyquinazolin-4-yl)-alpha-naphthalenylamine

To a 25 mL flask with 10 ml of abs. EtOH is added 0.137 g of 4-chloro-6,7-dimethoxyquinazoline and 0.087 g of 1-aminonaphthalene. The solution is heated to reflux whereupon the insoluble materials dissolve. After 5 minutes at reflux a precipatate forms. The solution is allowed to stir an additional 10 min before cooling and isolation of the product as the hydrochloride salt by simple filtration. High-vacuum drying of the solid provided analytically pure (6,7-dimethoxy-quinazolin-4-yl)-alpha-naphthalenylamine (0.142 g, white powder, m.p. 271°–273° C.

EXAMPLE 37

4-(m-chlorophenoxy)-6.7-dimethoxyquinazoline

THF (5 ml) and Nail (60% disp in oil, approx. 28 mg) is added to a dry flask maintained under inert atmosphere at room temperature. m-Chlorophenol (0.09 g) is added as a soln. in THP (1 mL) and stirring is continued until the solution became clear. 4-Chloro-6,7-dimethoxyquinazoline is added all at once (as the solid) and stirring was maintained overnight at RT. The solution is partitioned between $CH_2CL_2$ and 5% NaOH. The organic layer is washed with, brine, dried ($Na_2SO_4$) and concentrated. Flash column chromatography (40% EtOAc/Hex) provided the pure compound. An analytical sample is obtained by recrystallization from EtOAc/Hex to provide 4-m-chlorophenoxy)-6,7-dimethoxyquinazoline (0.05 g, white needles, m.p. 152°–153° C.

EXAMPLE 38

The above examples may be followed to prepare any of the desired compounds of this invention. A representative list of compounds which may be prepared are shown below in Table X.

TABLE X 3-(thien-3-yl)-6,7-dimethylquinoline, m.p. 132°–138° C.

3-(1-cyclopent-1-enyl)-6,7-dimethoxyquinoline hydrochloride, m.p. 213°–215° C.

3-cyclopentyl-6,7-dimethoxyquinoline hydrochloride, m.p. 213.5°–215° C.

4-(3-phenylpropyloxy)-6,7-dimethoxyquinoline, m.p. 90°–91.5° C.

3-(thien-3-yl)-6,7-dimethoxy-2(1H)-quinolone, m.p. 264°–266° C.

3-(thien-3-yl)-6,7-dimethoxyquinoline-N-oxide, m.p. 207°–208° C.

3-(2-chlorothien-5-yl)-5,7-dimethoxyquinoline, m.p. 153°–154° C.

3-(3-fluoro-4-methoxyphenyl)-6,7-dimethoxyquinoline, m.p. 165.5°–167° C.

3-phenyl-4-carboxy-6,7-dimethoxyquinoline, m.p. 259°–262° C.

3-(3-fluorophenyl)-6,7-dimethoxyquinoline, m.p. 156°–158° C.

4-(2-phenylethoxy)-6,7-dimethoxyquinoline, m.p. 117.5°–118.5° C.

3-(4-methoxybenzyloxy)-6,7-dimethoxyquinoline, m.p. 115.5°–118° C.

3-(3-fluoro-4-methoxyphenyl)-7-fluoroquinoline, m.p. 138°–140.5° C.

2-chloro-3-(thien-3-yl)-6,7-dimethoxyquinoline, m.p. 138.5°–139.5° C.

2-methyl-3-(thien-3-yl)-6,7-dimethoxyquinoline, m.p. 132°–132.5° C.

3-(thien-3-yl)-5-fluoroquinoline, m.p, 87.5°–89° C.

ethyl 4-(6,7-dimethoxyquinolin-3-yl)benzoate, m.p. 165°–166° C.

4-phenylpropyl-6,7-dimethoxyquinoline hydrochloride, m.p. 144°–147° C.

3-(thien-3-yl)-5,7-dimethylquinoline, m.p. 109.50°–111° C.

3-(5-chlorothien-2-yl)-6,7-dimethylquinoline, m.p. 131.5°–132.5° C.

3-(3-fluoro-4-methoxyphenyl)-7-methoxy4(1H)-quinolone, m.p. 291°–293° C.

3-(3-fluoro-4-methoxyphenyl)-5,7-dimethylquinoline, m.p. 109°–110° C.

3-(thien-3-yl)-6,7-difluoroquinoline, m.p. 141.5°–143.5° C.

3-benzyloxy-6,7-dimethoxyquinoline, m.p. 146.5°–148.5° C.

3-(2-methoxypyrid-5-yl)-6,7-dimethoxyquinoline, m.p. 170.5°–171.5° C.

3-cyclohexylethyl-6,7-dimethoxyquinoline (oil) (Calc'd/Fnd; C: 76.22175.10; H: 8.42/8.30; N: 4.68/4.60)

4-[3-(3-fluorophenyl)quinolin-6-yl]benzoic acid, m.p.>285° C.

2-phenyl-1-[3-(3-fluorophenyl)quinolin-6-yl)ethylene, m.p. 157.5°–159° C.

ethyl-4-[3-(3-fluorophenyl)quinolin-6-yl]benzoate, m.p. 168°–170° C.

methyl-3-[3-(3-fluorophenyl)quinolin-6-yl]propanoate, m.p. 83°–85° C.

methyl-3-[3-(3-fluorophenyl)quinolin-6-yl]propanoate, m.p. 184°–186° C.

3-(3-fluorophenyl)-6-(thien-3-yl)quinoline, m.p. 122°–124° C.

1-phenyl-2-[3-(3-fluorophenyl)quinolin-5-yl]ethylene, m.p. 101°–102° C.

3-(3-fluorophenyl)-6-methoxycarbonylquinoline, m.p. 196°–196.5° C.

3-(3-fluorophenyl)quinoline-6-carboxylic acid, m.p. 283°–284° C.

3-(3-fluorophenyl)-6-(N-ethylaminocarbonyl)quinoline, m.p. 184°–185° C.

1-dimethylamino-3-[3-(3-fluorophenyl)quinolin-6-yl]-2-propyne, m.p. 73°–74° C.

N-ethyl-3-[3-(3-fluorophenyl)quinoline-5-yl] propionamide, m.p. 147.5°–149.5° C.

4-[3-(3-fluorophenyl)quinolin-5-yl]benzoic acid, m.p.>280° C.

N-ethyl-3-[3-(3-fluorophenyl)quinoline-6-yl] propionamide, m p. 141°–142.5° C.

methyl-3-[3-(3-fluorophenyl)quinolin-5-yl]propenoate, m.p. 128°–130° C.

3-(3-fluorophenyl)-5-(thiophen-3-ylquinoline, m.p. 102°–103.5° C.

1-dimethylamino-313-(3-fluorophenyl)quinolin-6-yl] propane dihydrochloride, m.p. 194°–198° C.

1-[3-(3-fluorophenyl)quinolin-6-yl]-1-hexyne hydrochloride, m.p. 165°–169° C.

methyl-3-[3-(3-fluorophenyl)quinolin-5-yl]propanoate hydrochloride, m.p. 196°–198° C.

ethyl-4-[3-(3-fluorophenyl)quinolin-5-yl]benzoate, m.p. 132°–134° C.

1-[3-(3-fluorophenyl)quinolin-6-yl]n-hexane hydrochloride, m.p. 147.5°–149.5° C.

1-[3-(3-fluorophenyl)quinolin-5-yl]-1-hexyne hydrochloride, m.p. 168°–170.5° C.

1-[3-(3-fluorophenyl)quinolin-5-yl]-n-hexane hydrochloride, m.p. 141°–144° C.

3-[3-(3-fluorophenyl)quinolin-5-yl]propanoic acid, m.p. 249°–251° C.

N-(2-Phenylethyl)-3-[3-(3-fluorophenyl)-quinolin-5-yl] propionamide, m.p. 137.5°–140° C.

1-dimethylamino-3-[3-(3-fluorophenyl)quinolin-5-yl] propane dihydrochloride, m.p. 193°–198° C.

1-dimethylamino-3-[3-(3-fluorophenyl)quinolin-5-yl]-2-propane dihydrochloride, m.p. 77°–77.5° C.

3-(3-fluorophenyl)-5-(N-ethylaminocarbonyl)quinoline, m.p. 227°–227.5° C.

3-(3-fluorophenyl)-5-methoxycarbonylquinoline, m.p. 144°–145.5° C.

3-(3-fluorophenyl)quinolin-5-carboxylic acid, m.p. >280° C. (dec)

N-(2-phenylethyl)-3-[3-(3-fluorophenyl)quinolin-6-yl] propionamide, m.p. 139.5°–140° C.

3-(3-fluorophenyl)-7-(thien-3-yl)quinoline, m.p. 186°–187.5° C.

3-[3-(3-fluorophenyl)quinolin-6-yl]propanoic acid, m.p. 138.5°–141° C.

ethyl-4-[3-(3-fluorophenyl)quinolin-7-yl]benzoate, m.p. 134°–136° C.

methyl-3-[3-(3-fluorophenyl)quinolin-7-yl]propenoate, m.p. 164°–166° C.

3-(3-fluorophenyl)-7-methoxycarbonylquinoline, m.p. 163.5°–165° C.

1-[3-(3-fluorophenyl)quinolin-7-yl]hexyne hydrochloride, m.p. 183°–185° C.

3-(3-fluorophenyl)quinolin-7-carboxylic acid, m.p. >250° C.

4-[3-(3-fluorophenyl)quinolin-7-yl]benzoic acid hydrochloride, m.p.>250° C.

3-(3-fluorophenyl)-7-(N-ethylaminocarbonyl)quinoline, m.p. 193°–195° C.

N-(2-phenylethyl)-3-[3-(3-fluorophenyl)quinolin-7-yl] propionamide, mp. 157°–158.5° C.

3-[3-(3-fluorophenyl)quinolin-7-yl]propanoic acid hydrochloride, m.p.>250° C.

N-ethyl-3-[3-(3-fluorophenyl)quinolin-7-yl] propionamide, mp. 148°–149.5° C.

methyl-3-[3-(3-fluorophenyl)quinolin-7-yl]propanoate, m.p. 111.5°–113° C.

1-dimethylamino-3-[3-(3-fluorophenyl)quinolin-7-yl] propane dihydrochloride, m.p. 225.5°–228° C.

1-[3-(3-fluorophenyl)quinolin-7-yl]-n-hexane hydrochloride, m.p. 158°–160° C.

1-dimethylamino-3-[3-(3-fluorophenyl)quinolin-7-yl]-2-propyne, m.p. 86.5°–88.5° C.

3-(3-fluorophenyl)-6-carboxamidoquinoline, m.p. 225°–227° C.

5-[3-(3-fluorophenyl)quinolin-6-oxy]pentanoic acid, m.p. 216°–217° C.

3-(3-fluorophenyl)-6-[1 -(1-pyrrolidin-1-yl)-propan-3-yl] quinoline dihydrochloride, m.p. 238°–242° C.

3-(3-fluorophenyl)-7-(1-diethylamino-propan-3-yl) quinoline dihydrochloride, mp. 219°–222° C.

3-(3-fluorophenyl)-7-(1-diethylamino-2-propyn-3-yl) quinoline, m.p. 84°–86° C.

3-(3-fluorophenyl)-6-(1-diethylamino-propan-3-yl) quinoline dihydrochloride, m.p. 237°–241° C.

3-(3-fluorophenyl)-6-[1-(1-methylpiperazin-4-yl)propan-3-yl]quinoline trihydrochloride, m.p. 245°–248° C. (dec)

3-(3-fluorophenyl)-7-[1-(1-methylpiperazin-4-yl)propan-3-yl]quinoline trihydrochloride, m.p. >280° C.

3-(3-fluorophenyl)-6-(1-diethylamino-2-propyn-3-yl) quinoline dihydrochloride, m.p. 208°–211° C. (dec)

3-(3-fluorophenyl)-7-[1-(morpholin-4-yl)-propan-3-yl] quinoline dihydrochloride, m.p. 190°–193° C. (dec)

3-(3-fluorophenyl)-6-[1-(morpholin-4-yl)-propan-3-yl] quinoline dihydrochloride, m.p. 267°–270° C. (dec)

3-(3-fluorophenyl)-7-[1-(4methylpiperazin-1-yl)-2-propyn-3-yl]quinoline, m.p. 139.5°–141° C.

3-(3-fluorophenyl)-7-[1-(morpholin-4-yl)-2-propyn-3-yl] quinoline, mp. 137.5°–140° C. (dec)

3-(3-fluorophenyl)-6-[1-(morpholin-4-yl)-2-propyn-3-yl] quinoline, m.p. 134°–136° C. (dec)

3-(3-fluorophenyl)-7-[1-(1-pyrrlidino)-propan-3-yl] quinoline dihydrochloride, m.p. 245°–248° C. (dec)

3-(3 -fluorophenyl)-6-[1-(1-pyrollidino)-2-propyn-3 -yl] quinoline dihydrochloride, m.p. 214°–216° C. (dec)

3-(3-fluorophenyl)-7-[1-(1-pyrollidino)-2-propyn-3-yl] quinoline, m.p. 84°–87° C.

3-(3-fluorophenyl)-6-[1-(4-methylpiperazin-1 -yl)-2-propyn-3-yl]quinoline, m.p. 132°–134° C.

3- (3-fluorophenyl)-6-[4-(N,N-dimethylamino)butyloxy] quinoline dihydrochloride, m.p. 245°–248° C.

3-(3-fluorophenyl)-6-(1-hydroxy-2-propyn-3-yl) quinoline, m.p. 159°–160° C.

3-(3-fluorophenyl)-6-(4-hydroxy-butoxy)quinoline, m.p. 84°–86° C.

3-(3-fluorophenyl)-6-[1-(t-butyldimethylsilyloxy)-2-propyn-3-yl]quinoline, m.p. 100.5°–102° C.

methyl-5-[3-(3-fluorophenyl)quinolin-6-oxy]pentanoate, m.p. 70°–71° C.

3-(3-fluorophenyl)-6-(4-chlorobutoxy)quinoline hydrochloride, m.p. 179°–182.5° C.

3-(3-fluorophenyl)-7-[(2s)-2,3-dihydroxypropoxy-2-propyn-3-yl]quinoline hydrochloride, m.p. 170°–173° C.

6,7-dimethoxy-3-p-tolyloxyquinoline, m.p. 215°–217° C. (dec)

6,7-dimethoxy-3-phenoxyquinoline, m.p. 224°–226° C.

5,7-dimethoxy-3-phenoxyquinoline, m.p. 201°–203° C.

methyl 3-[3-(3-fluorophenyl)quinolin-6-yl]propenoate, m.p. 184°–186° C.

ethyl 4-[3-(3-fluorophenyl)quinolin-6-yl]benzoate, m.p. 168°–170° C.

2-phenyl-6,7-dimethylquinoxaline, m.p. 128°–131° C.

2-(4-methoxyphenyl)-6,7-dimethoxyquinoxaline hydrochloride, m.p. 212°–16° C.

2-(thien-3-yl)-6,7-dimethoxyquinoxaline hydrochloride, mp. 228°–231° C.

2-(thien-3-yl)quinoxaline, m.p. 87.5°–89° C.

2-phenyl-6,7-dimethoxyquinoxaline hydrochloride, m.p. 200° C.

6,7-dimethyl-2-(thien-3-yl)-quinoxaline, m.p. 142°–143.5° C.

2-phenyl-6,7-diethoxyquinoxaline hydrochloride, m.p. 180°–185° C.

2-(4-methoxyphenyl)-6,7-dimethoxyquinoxaline-4-N-oxide, m.p. 224°–226° C.

2-phenyl-6,7-dimethoxyquinoxaline-4-N-oxide, m.p. 219°–222° C.

2-phenyl-6,7-dimethylquinoxaline, m.p. 128°–131° C.

2-phenyl-6,7-dichloroquinoxaline, m.p. 158°–160° C.

2-phenyl-6,7-dimetoxyquinoxaline, m.p. 200° C.

2-phenyl-6,7-diethoxyquinoxaline, m.p. 180°–185° C.

2-phenethyl-6,7-diethoxyquinoxaline, m.p. 148°–155° C.

2-(thien-3-yl)-6,7-dimethylquinoxaline, m.p. 142°–143.5° C.

2-(thien-3-yl)-6,7-diethoxyquinoxaline, mp. 217°–224° C.

2-(5-chlorothien-2-yl)-6,7-diethoxyquinoxaline, m.p. 189°–194° C.

2-(5-chlorothien-2-yl)-6,7-dimethoxyquinoxaline, m.p. 218°–225° C.

2-(5-fluorothien-2-yl)-6,7-diethoxyquinoxaline, 2-(thien-2-yl)-6,7-diethoxyquinoxaline, 2-(thien-2-yl)-6,7-dimethoxyquinoxaline, m.p. 214°–220° C.

2-(thien-2-yl)-6,7-dicarboxyquinoxaline, 6,7-dimethyl-2-[4-1-tetrazol-5-yl)phenyl]quinoxaline, m.p. 278°–280° C. (dec.)

6,7-dimethyl-2-[5-(5-chloro-2-thien-2-yl)-2-thienyl] quinoxaline, m.p. 180°–183° C.

6,7-dimethyl-2-[5-(5-chloro-2-thien-2-yl)-2-thienyl] quinoxaline, m.p. 174°–177° C.

6,7-dimethyl-2-[4-(1-methyl-tetrazol-5-yl)phenyl] quinoxaline, m.p. 235°–238° C.

2-(3-fluoro-4-methoxy-phenyl)-7-(4-pyridyl)quinoxaline, m.p. 173°–175° C.

2-(3-fluoro-4-methoxy-phenyl)-6-(-pyrid-4-yl) quinoxaline, m.p. 210°–216° C.

2-(5-chloro-2-thien-2-yl)-7-(4-pyridyl)quinoxaline, m.p. 214°–215° C.

2-(5-chloro-2-thien-2-yl)-6-(pyrid-4-yl)quinoxaline, m.p. 260°–263° C.

7-(4-pyridyl-2-(3-thien-3-yl)quinoxaline, m.p. 210°–212° C.

6-(pyrid-4-yl)-2-(3-thienyl)quinoxaline, m.p. 234°–236° C.

2-(3-chloro-4methoxyphenyl)pyrido[3,4-b]pyrazine, 3-5-chlorothien-2-yl)pyrido[2,3-b]pyrazine, m.p. 194°–196° C.

2-3-fluoro-4-methoxyphenyl)pyrido[3,4-b]pyrazine, m.p. 214°–216° C.

2-3,4-dimethoxyphenyl)pyrido[3,4-b]pyrazine, m.p. 124°–127° C.

2-5-chlorothien-2-yl)pyrido[3,4-b]pyrazine, m.p. 203°–206° C.

2-(thien-2-yl)pyrido[3,4-b]pyrazine, 2-(thien-3-yl)pyrido[3,4-b]pyrazine, 2-(5-chlorothien-3-yl)pyrido[3,4-b]pyrazine, 2-(3-fluoro4-methoxyphenyl)thienyl[3,4-b]pyrazine, m.p. 187°–189° C.

3-(3'-thien-3-yl)-7-methoxy-pyrido-2,3b)-pyrazine, m.p. 215°–220° C.

7-(3'-thien-3-yl)pyrido-(2,3b)-pyrazine, m.p. 171°–173° C.

7-(3'-thien-3-yl)-2,3-dimethylpyrido-(2,3b)-pyrazine, m.p. 200°–205° C. (dec)

3-(3'-thien-3-yl)-7-bromo-pyrido-2,3b)-pyrazine, m.p. 205°–206.5° C.

2-(3,4-dimethoxyphenyl)pyrido[3,4-b]pyrazine, m.p. 124°–127° C.

3-(5-chloro-2-thien-2-yl)pyrido[2,3-b]pyrazine, m.p. 194°–196° C.

3-(3-fluoro-4-methoxyphenyl)pyrido[2,3-b]pyrazine, m.p. 217°–219° C.

2-(3-fluoro-4-methoxypehenyl)pyrido[3,4-b]pyrazine, m.p. 214°–216° C.

2-(5-chloro-2-thien-2-yl)pyrido[3,4-b]pyrazine, m.p. 203°–206° C.

6,7-dimethoxy-4-naphthalen-2-ylethynylquinazoline, m.p. 158°–161° C.

4-(4-hydroxyphenyl)-6,7-dimethoxyquinazolinehydrochloride, m.p.>270° C. (dec)

4-(naphthalen-1-yl)-6,7-dimethoxyquinazoline, m.p. 144°–147° C.

4-(naphthalen-2-yl)-6,7-dimethoxyquinazoline, m.p. 115°–118° C.

4-phenylacetylenyl-6,7-dimethoxyquinazoline, m.p. 146°–148° C.

4-(3-fluoro-4-methoxyphenyl)-6,7-dimethoxyquinazoline, m.p. 207°–210° C.

4-(3-phenylphenyl)-6,7-dimethoxyquinazoline, m.p. 160°–163° C.

4-(2-phenylethylenyl)-6,7-dimethoxyquinazoline, m.p. 168°–169° C.

4-(2-methoxypyridin-5-yl)-6,7-dimethoxyquinazoline, m.p. 175°–176° C.

4-(1-benzyl-indol-3-yl)-6,7-dimethoxyquinazoUne, m.p. 148°–150° C.

4-(indol-3-yl)-6,7-dimethoxyquinazoline, m.p.>240° C. (dec)

4-(1-methylindol-3-yl)-6,7-dimethoxyquinazoline hydrochloride, m.p.>230° C. (dec)

4-(1-methylsulphonylindol-3-yl)-6,7-dimethoxyquinazoline, m.p.>220° C. (dec)

4-(4-phenylpiperidin-1 -yl)-6,7-dimethoxyquinazoline, m.p. 150°–151° C.

4-[4-(3-chlorophenyl)piperazin-1-yl]-6,7-dimethoxyquinazoline, m.p. 155°–156° C.

4-(N-methyl-3,4,5-trimethoxyanilino)-6,7-dimethoxyquinazoline, m.p. 149°–151° C.

(+–)-4-(2-methyl-1,2,3,4-tetrahydroquinolin-1-yl)-6,7-dimethoxyquinazoline hydrochloride, m.p. 198°–201° C. (dec)

4-(1,2,3,4-tetrahydroquinolin-1-yl)-6,7-dimethoxyquinazoline hydrochloride, m.p. 195°–197° C. (dec)

4-(N-methyl-4-methoxy-anilino)-6,7-dimethoxyquinazoline hydrochloride, m.p. 202°–265° C.

4-(N-methyl-4-chloro-anilino)-6,7-dimethoxyquinazoline hydrochloride, m.p. 220°–222° C.

4-(2,3-dihydroindol-1-yl)-6,7-dimethoxyquinazoline hydrochloride, m.p. 226°–229° (dec)

(6,7-dimethoxyquinazolin4-yl)methyl-(3-trifluoromethylphenyl)amine hydrochloride, m.p. 240°–243° C.

(3-chlorophenyl)-(6,7-dimethoxyquinazolin-4-yl) methylamine hydrochloride, m.p. 235°–237° C.

(3-chlorophenyl)methylquinazolin-4-yl-amine hydrochloride, m.p. 233°–235° C.

6,7-dimethoxy-4-naphthalen-1-yl-ethynylquinazoline, m.p. 175°–177° C.

4-(thien-3-yl)-6,7-dimethoxyquinazoline, m.p. 148.5°–151.5° C.

4-benzyl-6,7-dimethoxyquinazoline, m.p. 122.5°–125° C.

2-(4-methylphenyl)-3-methyl-4(3H)quinazolinone, m.p. 139°–141° C.

2-(4-methoxyphenyl)quinazolin-4(3H)-one, m.p. 244°–247° C.

2-(4-methoxyphenyl)-6,7-dimethoxyquinazolin-4(3H)-one, m.p. 288°–291° C.

(6,7-dimethoxyquinazolin-4-yl)-5-indazol-5-yl hydrochloride, m.p. 261°–263° C. (dec)

N-phenyl-N-(6,7,8-trimethoxyquinazolin-4-yl) methylamine, m.p. 122.5°–124.5° C.

(6,7-dimethoxyquinazolin-4-yl)-N-phenylethylamine hydrochloride, m p. 227°–230° C. (dec)

benzyl-(6,7-dimethoxyquinazolin-4-yl)phenylamine hydrochloride, m.p. 269°–271 ° C.

(6-chloroquinazolin-4-yl)methylphenylamine, m.p. 106°–108° C.

(3-chloro-phenyl)-(6,7-dimethoxyquinazolin-4-yl) ethylamine hydrochloride, m.p. 261°–263° C.

(6,7-dimethoxyquinazolin-4-yl)methyl-p-tolyl-amine hydrochloride, m.p. 230°–234° C. (dec)

benzyl-(6,7-dimethoxyquinazolin-4-yl)amine, m.p. 220°–225° C.

(4-methoxybenzyl)-(6,7-dimethoxyquinazolin-4-yl) amine, m.p. 194°–198° C.

(3,5-dimethoxybenzyl)-(6,7-dimethoxyquinazolin-4-yl) amine hydrochloride, m.p. 265°–269° C.

4-(3,4,5-trimethoxyphenyl)-6,7-dimethoxyquinazoline, m.p. 228°–232° C.

methylphenyl-(9H-purin-6-yl)amine, m.p. 229°–232° C.

(quinazolin-4-yl)-N-phenylmethylamine hydrochloride, m.p. 242°–246° C. (dec)

(6,8-dimethylquinazolin-4-yl)-N-phenylmethylamine, m.p. 120°–121° C.

(6,7-dimethoxyquinazolin-4-yl)-4-morpholin-4-yl-phenyl)amine hydrochloride, m.p. 231°–235° C. (dec)

4-(3-methoxythiophenoxy)-6,7-dimethoxyquinazoline, m.p. 139.5°–141.5° C.

4-[N-(indan-5-yl)amino]-6,7-dimethoxyquinazoline hydrochloride, m.p. 244°–246° C. (dec)

3-chlorophenyladenine hemi-hydrochloride, m.p. >260° C.

4-(3-chlorothiophenoxy)-6,7-dimethoxyquinazoline, m.p. 152°–153.5° C.

4-(3-aminopyrazolyl)-6,7-dimethoxyquinazoline hydrochloride, m.p. 262°–264° C. (dec)

4-(3,6-dioxananilino)-6,7-dimethoxyquinazoline hydrochloride, m.p. 267°–269° C. (dec)

$N^6$-(3,4,5-dimethoxyphenyl)adenine hydrochloride, m.p.>250° C.

6,7-dimethoxy-4-(α-naphthylamino)quinazoline hydrochloride, m.p.>250° C.

6,7-dimethoxy-4-(β-naphthylamino)quinazoline hydrochloride, m.p.>250° C.

4-(cyclohexylanilino)-6,7-dimethoxyquinazoline, m.p. 239°–244° C.

4-(3,4,5-trimethoxyanilino)-6,7-dimethoxyquinazoline hydrochloride, m.p. 260°–265° C.

6,7-dimethoxy-4-(N-methylanilino)quinazoline hydrochloride, m.p.>230° C.

4-(3-chlorophenoxy)-6,7-dimethoxyquinazoline, m.p. 152°–153° C.

(4-methoxyphenyl)methyl-(1H-pyrazolo[3,4-d] pyrimidin-4-yl)amine hydrochloride, m.p. 223°–226° C.

6-(thien-3-yl)-1,8-naphthyridin-2(1H)-one, m.p. 250°–250° C.

6-(4-methoxyphenyl)-1,8-naphthyridin-2(1H)-one, m.p. 251°–253° C.

7-(3,4-dimethoxyphenyl)pteridine, m.p. 198°–199° C.

7-(4-methoxyphenyl)pteridine, m.p. 210°–213° C.

7-(5-chloro-2-thien-2-yl)pteridine, m.p. 231 ° C. (dec)

7-(3-fluoro-4-methoxy-phenyl)pteridine 7-(5-chlorothien-2-yl)pteridine, m.p. 231° C. dec.), 7-(thien-2-yl)pteridine 5,6-dimethoxy-2-(2-phenylethenyl)benzothiazole, m.p. 133°–135° C.

methyl-(1H-pyrazole[3,4-d]pyrimidin-4-yl)-(3-trifluoromethylphenyl)amine, m.p. 226°–227° C.

3-benzyl-5-(thien-3-yl)pyridine, m.p. 81°–82° C.)

3-(thien-3-yl)-6,7-dimethoxyisoquinoline-N-oxide, m.p. 197°–200° C.

3-(thien-3-yl)-6,7-dimethoxyisoquinoline-N-oxide, m.p. 197°–200° C.

3-(thien-3-yl)-6,7-dimethoxy-1(2H)-isoquinolone, m.p. 213°–216° C.

4-(thien-3-yl)isoquinoline hydrochloride, m.p. 179°–183° C.

4-(4-methoxyphenyl)isoquinoline hydrochloride, m.p. 196°–199° C.

2-phenyl-6,7-dimethoxy-4H-3,1-benzoxazin-4-one, m.p. 198°–201° C.

3-(4-methoxyphenyl)-7-methoxy-1-naphthalenol, m.p. 155°–159° C.

1-phenylphthalazine, m.p. 139.5°–141° C.

(4-methoxyphenyl)methyl-(1H-pyrazolo[3,4-d] pyrimidin-4-yl)amine hydrochloride, m p. 223°–226° C.

EXAMPLE 39

The procedures described in the above examples may be followed to prepare the following representative compounds If TABLE XI.

TABLE XI 5-(6,7-Dimethoxy-quinolin-3-yl)-2-hydroxy-benzoic acid 5-(6,7-Dimethoxy-quinolin-3-yl)-2-methoxy-benzoic acid 5-(6,7-Dimethoxy-quinolin-3-yl)-2-methoxy-benzamide 5-(6,7-Dimethoxy-quinolin-3-yl)-2-hydroxy-benzamide 4-(6,7-Dimethoxy-quinolin-3-yl)-2-hydroxy-benzoic acid 8-Fluoro-6,7-dimethoxy-3-(4-methoxy-phenyl)-quinoline N-(6,7-Dimethoxy-quinolin-4-yl)-N-phenyl-methylamine N-(6,7-Dimethoxy-quinolin-4-yl)-aniline 5-(6,7-Dimethoxy-quinolazolin-4-yl)-2-hydroxy-benzoic acid 2-Benzyloxy-5-(6,7-dimethoxy-quinazolin-4-yl)-benzoic acid 5-(6,7-Dimethoxy-quinolazolin-4-yl)-2-methoxy-benzoic acid 5-(6,7-Dimethoxy-quinolazolin-4-yl)-2-hydroxy-benzamide 5-(6,7-Dimethoxy-quinolazolin-4-yl)-2-hydroxy-benzamide 4-(6,7-Dimethoxy-quinolazolin-4-yl)-2-hydroxy-benzoic acid 6,7-dimethoxy-4-(1-naphthylthio)-quinazoline 6,7-dimethoxy-4-(2-naphthylthio)-quinazoline 6,7-dimethoxy-4-(1-naphthyloxy)-quinazoline 6,7-dimethoxy-4-(2-naphthyloxy)-quinazoline 6,7-Dimethoxy-quinolazolin-4-yl)-2-naphthyl-ethylamine 6,7-dimethoxy-4-(naphthalene-2-sulfinyl)-quinazoline 6,7-dimethoxy-4-(naphthalene-2-sulfonyl)-qinazoline 4-(4-Methoxyphenyl)-7,8-dimethoxyisoquinoline 4-(3-Fluoro-4-methoxyphenyl)-7-chloroisoquinoline 4-(3-Fluoro-4-methoxyphenyl)-8-chloroisoquinoline 1-Anilinoisequinoline 1-(N-Methyl-3,4,5-trimethoxyanilino)isoquinoline Preparation of Pharmaceutical Compositions and Pharmacological Test Section Compounds within the scope of this invention exhibit significant activity as protein tyrosine kinase inhibitors and possess therapeutic value as cellular antiproliferative agents for the treatment of certain conditions including psoriasis, atherosclerosis and restenosis injuries. It is expected that the invention will be particularly applicable to the treatment of atherosclerosis. With regard to the treatment of some conditions, for example, atherosclerosis, certain people may be identified as being at high risk, for example, due to genetic, environmental or historical factors. Compounds within the scope of the present invention exhibit the modulation and/or inhibition of cell signaling, cell proliferation, cell inflammatory response, the control of abnormal cell growth and cell reproduction can and can be used in preventing or delaying the occurrence or reoccurrence of such conditions or otherwise treating the condition.

To determine the effectiveness of compounds of this invention, the following pharmacological tests described below, which are accepted in the art and recognized to correlate with pharmacological activity in mammals, are utilized. Compounds within the scope of this invention have been subjected to these various tests, and the results obtained are believed to correlate to useful cellular antiproliferative activity. The below described tests are useful in determining the EGF receptor kinase, PDGF receptor kinase and insulin receptor kinase inhibition activities of compounds disclosed herein. The results of these tests are believed to provide sufficient information to persons skilled in the pharmacological and medicinal chemistry arts to determine the parameters for using the studied compounds in one or more of the therapies described herein.

EGF-Receptor Purification

EGF-receptor purification is based on the procedure of Yarden and Schlessinger. A431 cells are grown in 80 $cm^2$ bottles to confluency ($2\times10^7$ cells per bottle). The cells are washed twice with PBS and harvested with PBS containing 11.0 mmol EDTA (1 hour at 37° C., and centrifuged at 600g for 10 minutes. The cells arc solubilized in 1 ml per $2\times10^7$ cells of cold solubilization buffer (50 mmol Hepes buffer, pH 7.6, 1% Triton X-100, 150 mmol NaCl, 5 mmol EGTA, 1 mmol PMSF, 50 μg/ml aprotinin, 25 mmol benzamidine, 5 μg/ml leupeptic, and 10 μg/ml soybean trypsin inhibitor) for 20 minutes at 4° C. After centrifugation at 100,000 g for 30 minutes, the supernatant is loaded onto a WGA-agarose column (100 μl of packed resin per $2\times10^7$ cells) and shaken for 2 hours at 4° C. The unabsorbed material is removed and the resin washed twice with HTN buffer (50 mmol Hepes, pH 7.6, 0.1% Triton X-100, 150 mmol NaCl), twice with HTN buffer containing 1M NaCl, and twice with HTNG buffer (50 mmol Hepes, pH 7.6, 0.1% Triton X-100, 150 mmol NaCl, and 10% glycerol). The EGF receptor is eluted batchwise with HTNG buffer containing 0.5M N-acetyl-D-glucosamine (200 μl per $2\times10^7$ cells.). The eluted material is stored in aliquots at −70° C. and diluted before use with TMTNG buffer (50 mmol Tris-Mes buffer, pH 7.6, 0.1% Triton X-100, 150 mmol NaCl, 10% glycerol).

ATP and EGF Dependence of Autophosphorylation

WGA-purified EGF receptor from A431 cells (0.5 μg/assay is activated with EGF (0.85 μM) for 20 minutes at 4° C.. The assay is performed at 15° C. and initiated by addition of $Mg(Ac)_2$ (60 mmol), Tris-Mes buffer, pH 7.6 (50 mmol), [$^{32}$P]ATP (carrier free, 5 μCi/assay), and increasing concentrations of nonradioactive ATP. The assay is terminated after 10-sec by addition of SDS sample buffer. The samples are run on a 6% SDS polyacrylamide gel. The gel is dried and autoradiographed as described above. The relevant radioactive bands are cut and counted in the Cerenkov mode. The Km for ATP determined in this fashion is found to be 7.2 μ(M. With use of the 10-sec assay protocol, the EGF concentration dependence of EGF-RK autophosphorylation is determined.

Inhibition of EGF-R Autophosphorylation

A431 cells were grown to confluence on human fibronectin coated tissue culture dishes. After washing 2 times with ice-cold PBS, cells were lysed by the addition of 500 μl/dish of lysis buffer (50 mmol Hepes, pH 7.5,150 mmol NaCl, 1.5 mmol $MgCl_2$, 1 mmol EGTA, 10% glycerol, 1% triton X-100, 1 mmol PMSF, 1 mg/ml aprotinin, 1 mg/ml leupeptin) and incubating 5 minutes at 4° C. After EGF stimulation (500 μg/ml 10 minutes at 37° C.) immunoprecipitation was performed with anti EGF-R (Ab 108) and the autophosphorylation reaction (50 μl aliquots, 3 μCi [γ-$^{32}$P] ATP) sample was carried out in the presence of 2 or 10 μM of compound of the present invention, for 2 minutes at 4° C. The reaction was stopped by adding hot electrophoresis sample buffer. SDA-PAGE analysis (7.5% els) was followed by autoradiography and the reaction was quantitated by densitometry scanning of the x-ray films.

In order to test the present compounds for selective inhibition, the procedure is repeated using PDGF stimulation in place of EGF stimulation. "$IC_{50}$," as used below refers to the concentration of inhibitor mM) at which the rate of autophosphorylation is halved, compared with media containing no inhibitor.

Inhibition of PDGF-R Autophosphorylation

Lysate from NIH 3T3 cells was diluted one-third in Triton-free buffer and stimulated with 10 ng/ml PDGF for 30 minutes at 4° C. The equivalent of 1/15 of a 175-cm$^2$ plate of lysate was used per sample. The stimulated lysate was then immunoprecipitated with rabbit polyclonal anti-PDGF-receptor antibodies raised against a synthetic peptide from the COOH-terminal region (amino acids 1094–1106) or the human PDGF-receptor B-subunit and added to increasing concentrations of test compound of the present invention. After 10 minutes at 4° C., 10 μCi of [γ-$^{32}$P]ATP were added and further incubated for 10 minutes at 4° C. Samples were separated by SDS-PAGE on 6% gels.

Inhibition of Cell Proliferation as Measured by Inhibition Of DNA Synthesis

EGF receptor overexpressing (HER14) cells were seeded at $1\times10^5$ cells per well in 24-well Costar dishes pre-coated with human fibronectin (by incubating for 30 minutes at room temperature with 10 μg/0.5 ml/well). The cells were grown to confluence for 2 days. The medium was changed to DMEM containing 0.5 calf serum for 36–48 hours and the cells were then incubated with EGF (Toyobo, New York, N.Y.) (20 ng/ml), PDGF (Amgen) (20 ng/m 1) or serum (10% calf serum, FCS) and different concentrations of the compound of the present invention. [3H] thymidine, (NEN, Boston, Mass.) was added 16–24 hours later at 0.51 μCi/ml for 2 hours. TCA precipitable material was quantitated by scintillation counting (C Results of this assay are determined. "$IC_{50}$" of the concentration of inhibitor (nM) at which [$^3$H] thymidine incorporation is halved, compared with media containing no buffer is calculated As FCS contains a broad range of growth factors, the $IC_{50}$ values for PDGF should be lower than for FCS, indicating that the compounds of the present invention do not act as general inhibitors.

These results indicate that compounds within the scope of the invention inhibit the EGF and/or PDGF growth factor receptors selectively.

Cell Culture

Cells termed HER 14 and K721A (=DK) were prepared by transfecting NIH3T3 cells (clone 2.2) (From C. Fryling, NCI, NIH), which lack endogenous EGF-receptors, with cDNA constructs of wild-type EGF-receptor or mutant EGF-receptor lacking tyrosine kinase activity (in which Lys 721 at the ATP-binding site was replace by an Ala residue, respectively). All cells were grown in DMEM with 10% calf serum (Hyclone, Logan, Utah).

Further tests which show the effectiveness and selectivity of compounds of this invention to inhibit cell proliferation are as follows.

CSF-1R CELL-FREE AUTOPHOSPHORYLATION ASSAY

For a regular 28 tube assay (14 samples per 15 well gel):

In 2 ml eppendorf tube: 140 mg protein A sepharose (5 mg/sample)

Swell in 20 mM Hepes pH 7.5 and wash 2× in Hepes

Add 280 λα-CSF-1R (from rabbit 3: C1-3-?)

20 min RT shaking

Wash 3× in HNTG pH 7.5:20 mM Hepes 150 mM NaCl 0.1% triton X-100

10 % glycerol

In 15 ml tube: 2.8 ml lysate (100 λ/sample of lysate made from unstarved, subconfluent cfm Y cells)

lysis buffer: 20 mM Hepes 1.5 mM $MgCl_2$ 150 mM NaCl 1 mM EGTA

10% glycerol

1% triton X-100

Protease inhibitors added fresh:

PMSF: 8 mg/ml-2500× in 100% EtOH, store frozen, add 100λ/10 ml lysis buffer Aprotinin: 10 mg/ml=250× in $H_2O$, store frozen (expires in about 6 months), add 40λ/10 ml lysis buffer Leupeptin: 1 mg/ml=250× in $H_2O$, store frozen (expires in about 6 months), add 40λ/10 ml lysis buffer Add washed beads to stimulated lysate and incubate 90 min 4° C. on rotator or shaking (anywhere from 1 to 2.5 hours OK)

Meanwhile:

prepare 28 compound tubes:

make 40 mM solutions of compounds in 100% DMSO make serial dilutions in 50 mM Tris pH 7.5+10 mM $MnCl_2$ aliquot 10λ compound solution into each I ml eppendorf reaction tube waiting on ice, control blanks get 10λ buffer Wash beads 1× HNTG, 2×10 mM Tris pH 7.5 (can transfer beads to 2 ml eppendorf tube for washing)

Remove all liquid with gel loading pipette tip or Hamilton syringe

Add back 560λ 50 mM Tris pH 7.5+10 mM $MnCl_2$ (20λ/sample)

Dole out into waiting reaction tubes (approx. 28λ/tube using large bore tip)

Vortex, incubate 10 min on ice

Add 10λ ATP solution: 312λ 50 mM Tris pH 7.5+10 mM $MnCl_2$ 2.7λ cold ATP (stock of 10 mM in 50 mM Tris=20 μM final)

351 $^{32}$P-ATP (10 μCi/sample)

Vortex, incubate 10 min on ice

Add 45λ 2× SDS-sample buffer, heat 95° C. 6 min 7.5% SDS-PAGE, fix, dry, expose (usually 4 hrs)

*Note: it is important to keep lysate cold at all times: when thawing, don't use water which is too warm and use cold buffer for wash steps.

Ick Kinase: Immunoprecipitated from Jurkat lysate.[5,6]

A. Jurkat cells (human T-cell leukemia, ATCC clone #E6-1) were grown in suspension in RPMI 1640 medium with 10% fetal calf serum, 100 U/ml penicillin/streptomycin, and 2 mM L-glutamine in a 37° C. incubator at 5% $CO_2$.

B. Cells were grown to 1–1.5×$10^6$ cells/ml media, pelleted by centrifugation, and lysed in lysis buffer at $10^8$ cells/ml buffer (50 mM tris (pH 8), 150 mM NaCl, 5 mM EDTA, 10% glycerol, and 1% NP-40, to which fresh protease and phosphatase inhibitors were added as described above for A431 lysate). Lysates stored at −70° C.

C. Immunoprecipitation [#5264:12]: 3–4 mg Protein-A sepharose/sample washed 2×20 mM Hepes (pH 7.5). 1 ul α-lck antibody (prepared as polyclonals in rabbits using a peptide antigen corresponding to the N-terminal region of human lck) per sample added to the Protein-A and shaken 20 min at room temperature. After washing 3× HNTG, lysate from 2×$10^6$ cells was added to each sample, rotated 2 hr at 4° C., then washed 3× HNTG (2nd wash containing 0.5 N NaCl). If all samples contain identical concentrations of the enzyme, then the immuno-precipitation can be done in bulk and alloquoted to appropriate numbers of tubes prior to assay set-up.

D. Compound screening in the cell-free/ck kinase assay [#5264:12]: RPR compounds (40 mM stocks in DMSO) were initially screened at concentrations of 10 and 100 uM in samples containing Ick immuno-precipitated from 2×$10^6$ cells, 5 uM cdc2 (a $p34^{cdc2}$-derived synthetic peptide (N6-20) prepared by R. Howk, RPR)[7], 5 mM $MnCl_2$, 5 uM ATP and 30 uCi $g^{32}$p-ATp (6000Ci/mmol, NEN) in 20 mM hepes (pH 7.5) for 5 min at 30° C. Samples were analyzed by 5–15% SDS-PAGE and autoradiography as described for EGFR kinase assays.

E. Intact cell activation/inhibition studies[8,9] [#5264:31] :~5×$10^7$ cells per sample in 1 ml media were activated with either 10 ug a-CD3 (clone Cris 7, Biodesign) for 1 min at 37° C. or 20 ng PMA and 10 ug PHA for 20 min at 37° C. in the presence and absence of compound (added earlier so that the total time of compound incubation is 30 min). Incubations were terminated by centrifugation and lysis (as described). Samples were analyzed by immunoprecipitation (aPY (100 ul/$10^8$ cells), a-PLC (100 ul/$10^8$ cells), or azeta (20 ul/$10^8$ cells)), followed by SDS-PAGE and western blotting onto nitrocellulose and inimunoblotting using RC20 recombinant aPY-HRP Transduction Labs) and ECL (Amersham).

cAMP-dependent Protein Kinase (PKA) Assay[10]

Selectivity assay for compounds is performed as follows. Each sample contains 0.4 pmolar units PKA (from rabbit muscle, Sigma), 1 uM cAMP, 50 uM Tris-HCL (pH7), 10 mM MgAc, 50 ug BSA, 16 uM Kemptide substrate (specific cAMP kinase phosphate acceptor whose sequence corresponds to the pig liver pyruvate kinase phosphorlyation site), 16 uM ATP, 16 uCi $^{32}$P-ATP (6000Ci/mmol, NEN), +/− compound and $dH_2O$ to a final volume of 200 ul. Reactions proceed for 5 min. at 30° C., and are terminated by the addition of 100 ul 375 mM $H_3PO_4$. 50 ul each sample spotted onto Whatman P81 phosphocellulose filters, which are washed 3× (15 min.) in 75 mM $H_3PO_4$, followed by an acetone rinse and dry (Cerenkov) counting.

In view of the results of the above test, compounds of the present invention can be shown to be selective.

The preferred class of compounds exhibiting CSF-1 inhibition and lck Kinase inhibition are the 6,7-dialkoxy quinazolines, and most preferred are the 4-arylamino, 6,7-dimethoxyquinazolines. The most preferred lck inhibitory compound is 4-(3,4,5-trimethoxyphenylamino)-6,7-dimethoxyquinazoline, (m.p. 260°–265° C. (HCl)), which is prepared according to the procedure described in Example 36 using 1.6 g of 3,4,5-trimethoxyaniline and 0.2g of 4-chloro,-6,7-dimethoxyquinazoline, under similar reaction conditions. The most preferred CSF-1 inhibitory compound is 4-(N-methyl, N-phenylamino)-6,7-dimethoxyquinazoline, (m.p>230° C.(HCl)), which is prepared according to the procedure described in Example 36 using 140mg of N-methylaniline and 300 mg of 4-chloroquinazoline, under similar reaction conditions.

The following tables show examples of representative compounds of this invention and their test results as determined by the above inhibition of PDGF-R cell-free autophosphorylation procedure.

| COMPOUND | Inhibition of PDGF-R cell-free Autophosphorylation $IC_{50}$ ($\mu$M) |
|---|---|
| 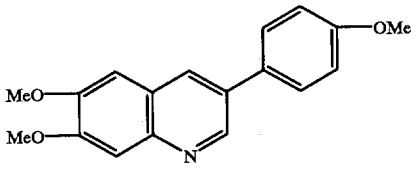 | 0.003–0.015 |
| 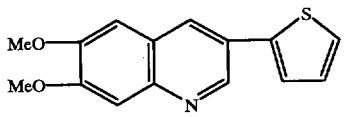 | 0.050–0.10 |
| 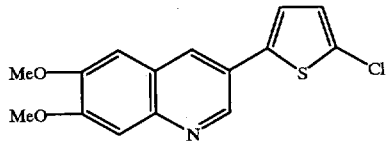 | 0.007 |

-continued
| | |
|---|---|
| 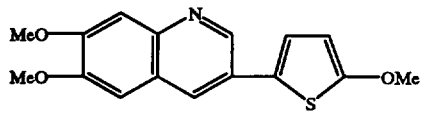 | 0.2–1 |
| 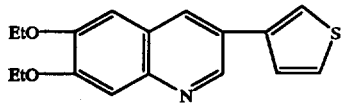 | 0.06–0.08 |
| 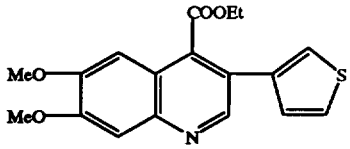 | 1.0–2.0 |
| 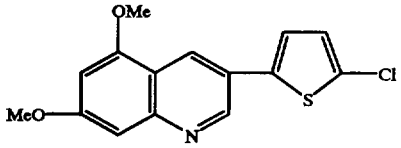 | 0.015 |
| 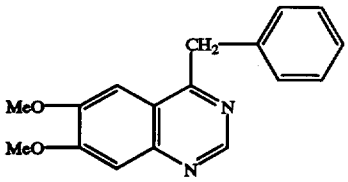 | 15–20 |
| 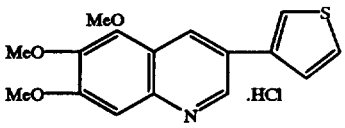 | 0.02 |
| 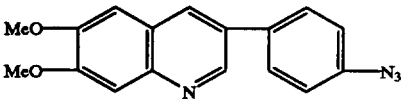 | 0.01 |
| 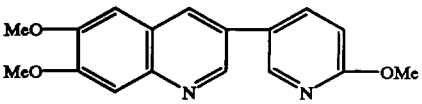 | 0.030–0.070 |
| 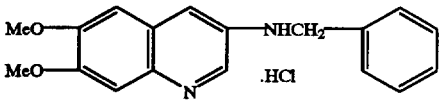 | 0.02–0.08 |
| 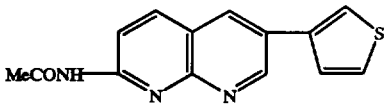 | 0.05–0.1 |
| 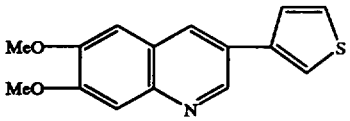 | 0.005–0.030 |

-continued
| | |
|---|---|
| 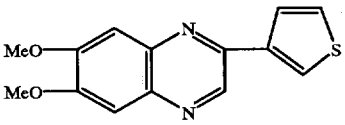 | 0.02–0.05 |
| 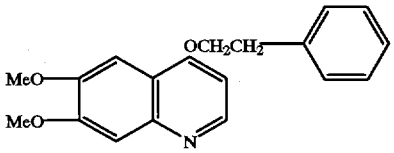 | 0.7–1.0 |
| 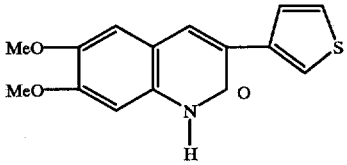 | 0.7–1.0 |
| 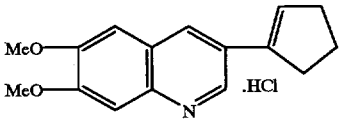 | 0.04 |
| 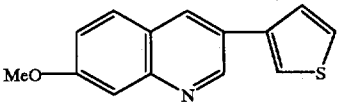 | 0.010–0.060 |
| 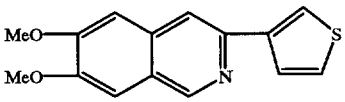 | 7–12 |
| 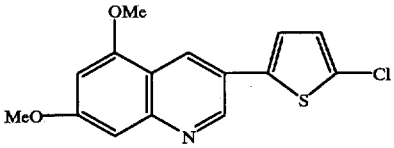 | 0.015 |
| 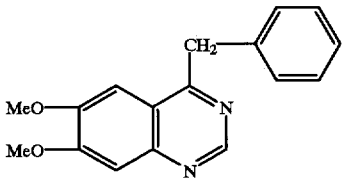 | 15–20 |
| 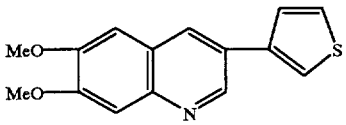 | 0.005–0.030 |
| 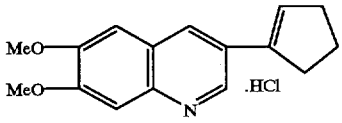 | 0.04 |

-continued
| | |
|---|---|
| 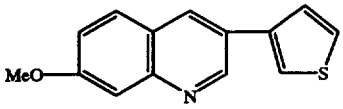 | 0.010–0.060 |
| 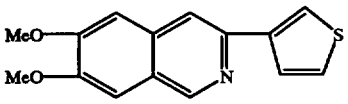 | 7–12 |
| 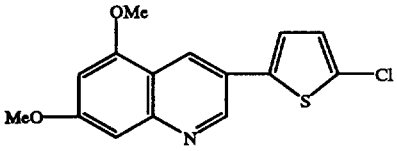 | 0.015 |
| 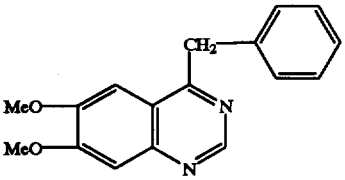 | 15–20 |
| 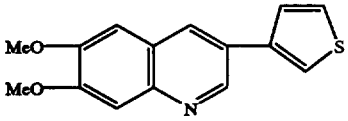 | 0.005–0.030 |
| 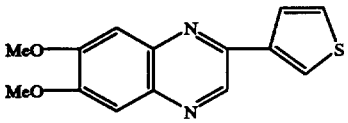 | 0.02–0.05 |
| 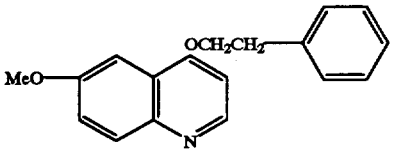 | 0.7–1.0 |
| 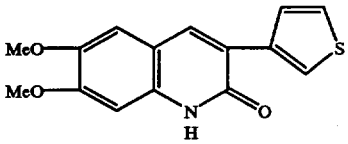 | 0.7–1.0 |
| 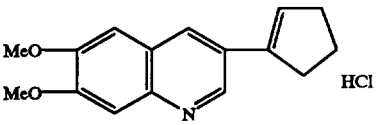 | 0.04 |
| 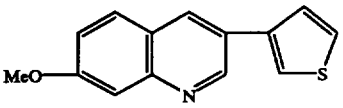 | 0.010–0.060 |

-continued
| | |
|---|---|
| 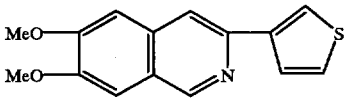 | 7–12 |
| 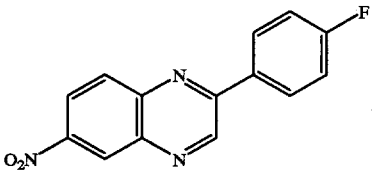 | >50 |
| 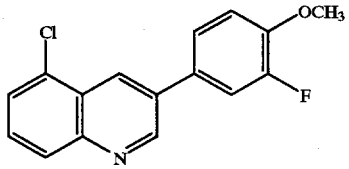 | 10–20 |
| 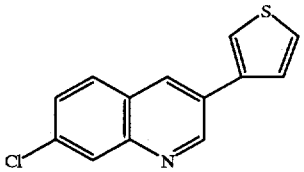 | 0.025–0.3 |
| 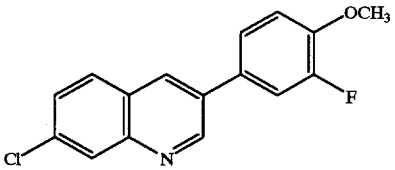 | 0.05–0.2 |
| 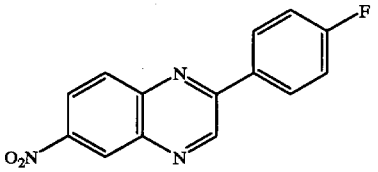 | >50 |
| 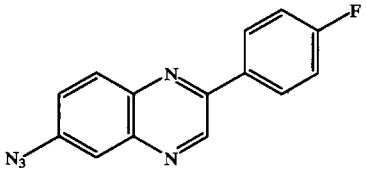 | >50 |
| 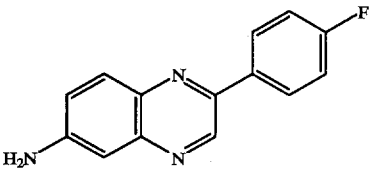 | 0.5–3 |

-continued
| | |
|---|---|
| 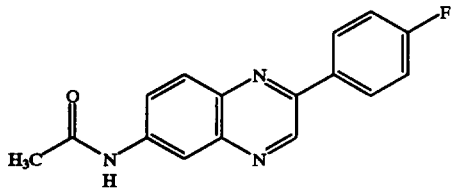 | 9 |
| 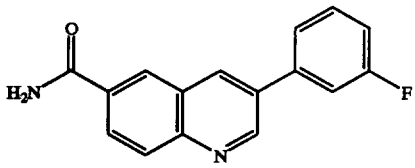 | 7 |
| 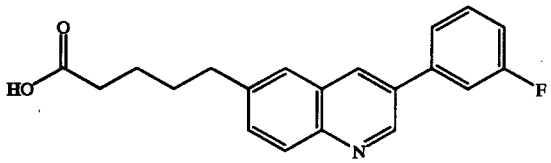 | 0.6 |
| 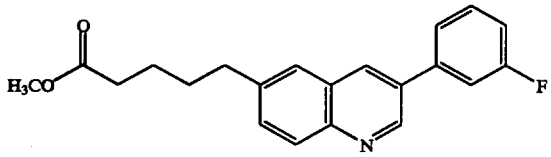 | 0.25 |
| 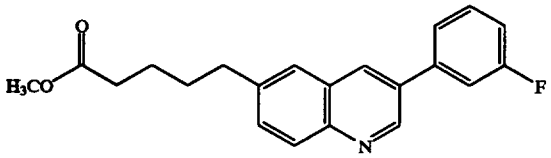 | 2 |
| 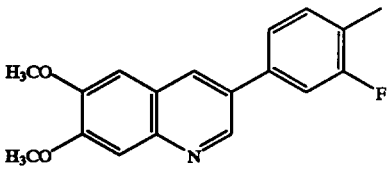 | 2 |
| 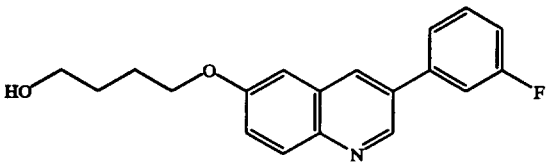 | <2 |
| 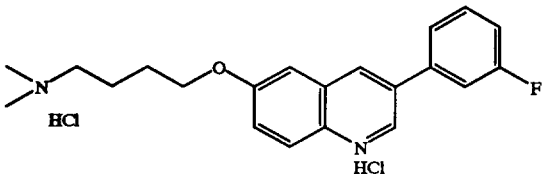 | <2 |

-continued
| 4-Substituted-6,7-di-methoxyquinazolines | EGF-R | PDGF-R |
|---|---|---|
| 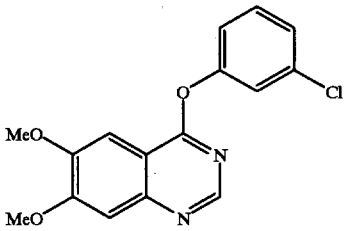 | 0.02 | 1.5 |
| 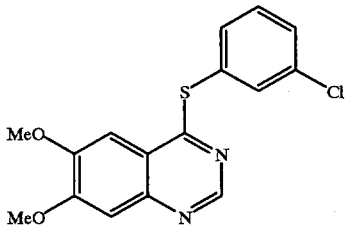 | 0.1 | >50 |
| 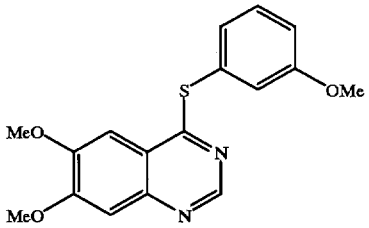 | 2 | |
| 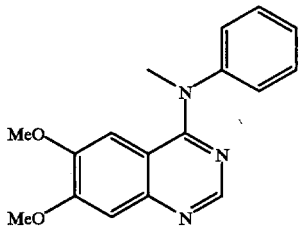 | 4.0 | 15 |
| 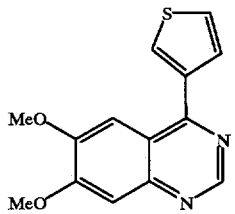 | — | 25 |
| 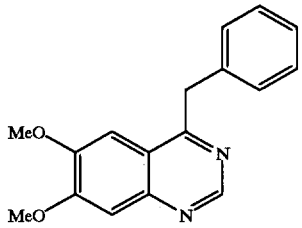 | 0.35 | 15 |

-continued

| | | |
|---|---|---|
| 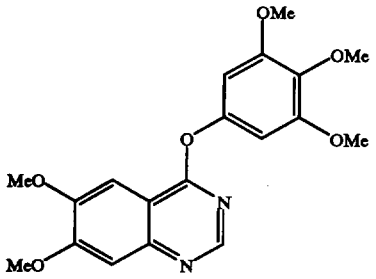 | — | 5–20 |
| 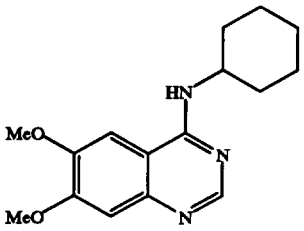 | <1.0 | >20 |
| 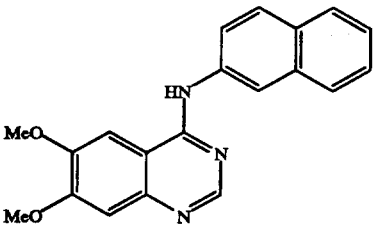 | 0.050 | 10 |
| 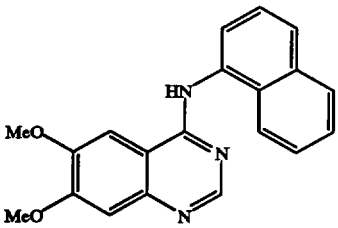 | 0.010 | 20 |

The results obtained by the above experimental methods evidence the useful protein tyrosine kinase inhibition properties of compounds within the scope of the present invention and possess therapeutic value as cellular antiproliferative agents. The above pharmacological test results may be used to determine the dosage and mode of administration for the particular therapy sought.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be Incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the for must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g or higher although it may be administered in several different dosage units from once to several times a day. Oral administration requires higher dosages.

We claim:

1. A method of inhibiting cell proliferation in a patient suffering from a disorder characterized by such proliferation comprising administering to a patient a pharmaceutical composition comprising an EGF and/or PDGF receptor inhibiting effective amount of a compound of the formula

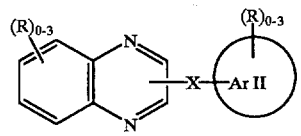

wherein:

Ar II is a substituted or unsubstituted mono- or bicyclic aryl or heteroaryl ring system of about 5 to about 12 atoms and where each monocyclic ring may contain 0 to about 3 hetero atoms, and each bicyclic ring may contain 0 to about 4 hetero atoms or at least one ring is a substituted or unsubstituted saturated carbocyclic of about 3 to about 7 atoms where each monocyclic ring may contain 0 to about 2 hetero atoms and where the hetero atoms are selected from N, O and S provided said hetero atoms are not vicinal oxygen and/or sulfur atoms and where the substituents may be located at any appropriate position of the ring system and are described by R;

X is $(CHR_1)_{0-4}$ or $(CHR_1)_m$—Z—$(CHR_1)_n$:

Z is O, NR', S, SO or $SO_2$:

m and n are 0–3 and m+n=0–3;

R substitution besides hydrogen independently includes alkyl, alkenyl, phenyl, aralkyl, aralkenyl, hydroxy, hydroxyalkyl, alkoxy, alkoxyalkyl, aralkoxy, acyloxy, halo, haloalkyl, nitro, amino, mono-and di-alkylamino, arylamino, carboxy, carboxyalkyl, carbalkoxy, carbaralkoxy, carbalkoxyalkyl, carbalkoxyalkenyl, aminoalkoxy, amido, mono- and di-alkylamido and N,N-cycloalkylamido, phenyl, halophenyl, thienyl, halothienyl, pyridyl, 1H-tetrazolyl or benzoyl;

R and R together may also be keto;

$R_1$ and R' are hydrogen or alkyl; or an N-oxide or a pharmaceutically acceptable salt thereof, in admixture with a pharmaceutically acceptable carrier.

2. A method according to claim 1 where the compound is described by:

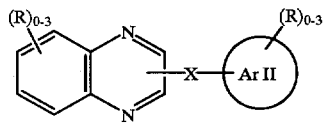

or

-continued

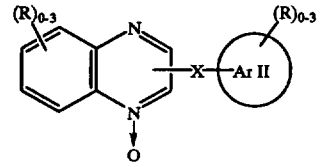

wherein

Ar II is phenyl, naphthyl, thienyl, cyclohexyl or cyclopentyl; and

X is a bond, methyl, ethyl, propyl or $(CHR_1)_m$—Z—$(CHR_1)_n$ where Z is O, S, SO, $SO_2$ or NR', and n and m are 0–1 and n+m is 0 or 1.

3. A method according to claim 2 comprising administering to said patient a pharmaceutically effective amount of a pharmaceutical composition containing, in admixture with a pharmaceutically acceptable carrier, a compound, or a pharmaceutically acceptable salt thereof, of the formulae:

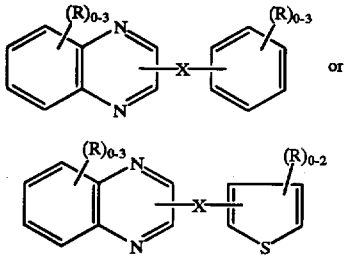

4. A method according to claim 3 where said compound is described by the formula:

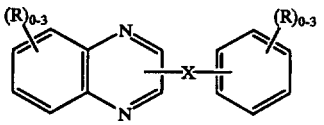

where:

X is a bond, O, NR', methyl, ethyl or propyl.

5. A method according to claim 3 where said compound is selected from the formula:

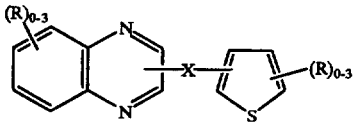

where:

X is a bond, O, NR', methyl, ethyl or propyl.

6. A method according to claim 4 where the compound administered is selected from:

2-phenyl-6,7-dimethylquinoxaline,
2-phenyl-6,7-dichloroquinoxaline,
2-phenyl-6,7-dimethoxyquinoxaline,
2-phenyl-6,7-dimethoxyquinoxaline-4-N-oxide.
2-phenyl-6,7-diethoxyquinoxaline,
2-(4-fluorophenyl)-6,7-diethoxyquinoxaline,
2-(4-fluorophenyl)-6,7-dimethylquinoxaline,
2-(4-fluorophenyl)-6-aminoquinoxaline,
2-(4-fluorophenyl)-6-acetamidoquinoxaline,
2-(4-methoxyphenyl)-6,7-dimethoxyquinoxaline,
2-phenethyl-6,7-diethoxyquinoxaline,
2-phenyl-6,7-dicarboxyquinoxaline,
2-(4-methoxyphenyl)-6,7-dimethoxyquinoxaline and
2-(4-methoxyphenyl)-6,7-dimethoxyquinoxaline-4-N-oxide.

7. A method according to claim 5 where the compound administered is selected from:

2-(thien-3-yl)-6,7-dimethylquinoxaline,
2-(thien-3-yl)-6,7-dimethoxyquinoxaline,
2-(thien-3-yl)-6,7-diethoxyquinoxaline,
2-(5-chlorothien-2-yl)-6,7-diethoxyquinoxaline,
2-(5-chlorothien-2-yl)-6,7-dimethoxyquinoxaline,
2-(5-fluorothien-2-yl)-6,7-diethoxyquinoxaline,
2-(thien-2-yl)-6,7-diethoxyquinoxaline,
2-(thien-2-yl)-6,7-dimethoxyquinoxaline and
2-(thien-2-yl)-6,7-dicarboxyquinoxaline.

8. A pharmaceutical composition for inhibiting cell proliferation comprising an EGF and/or PDGF receptor inhibiting effective amount of a compound or a pharmaceutically acceptable salt thereof selected from:

2-(thien-3-yl)-6,7-dimethylquinoxaline;
2-(thien-3-yl)-6,7-dimethoxyquinoxaline;
2-(thien-3-yl)-6,7-diethoxyquinoxaline;
2-(5-chlorothien-2-yl)-6,7-diethoxyquinoxaline;
2-(5-chlorothien-2-yl)-6,7-dimethoxyquinoxaline;
2-(5-fluorothien-2-yl)-6,7-diethoxyquinoxaline;
2-(thien-2-yl)-6,7-diethoxyquinoxaline;
2-(thien-2-yl)-6.7-dimethoxyquinoxaline;
2-(thien-2-yl)-6,7-dicarboxyquinoxaline;
2-phenyl-6,7-dimethylquinoxaline,
2-phenyl-6,7-dichloroquinoxaline,
2-phenyl-6,7-dimethoxyquinoxaline,
2-phenyl-6,7-dimethoxyquinoxaline-4-N-oxide,
2-phenyl-6,7-diethoxyquinoxaline,
2-(4-fluorophenyl)-6,7-diethoxyquinoxaline,
2-(4-fluorophenyl)-6,7-dimethylquinoxaline,
2-(4-fluorophenyl)-6-aminoquinoxalne,
2-(4-fluorophenyl)-6-acetamidoquinoxaline,
2-(4-methoxyphenyl)-6,7-dimethoxyquinoxaline,
2-phenethyl-6,7-diethoxyquinoxaline,
2-phenyl-6,7-dicarboxyquinoxaline
2-(4-methoxyphenyl)-6,7-dimethoxyquinoxaline and
2-(4-methoxyphenyl)-6,7-dimethoxyquinoxaline4-N-oxide in admixture with a pharmaceutically acceptable carrier.

9. A compound selected from:

2-phenyl-6,7-dimethylquinoxaline,
2-phenyl-6,7-dichloroquinoxaline,
[2-phenyl-6,7-dimethoxyquinoxaline,
2-phenyl-6,7-diethoxyquinoxaline,]
2-(4-fluorophenyl)-6,7-diethoxyquinoxaline,
2-(4-fluorophenyl)-6,7-dimethylquinoxaline,
2-(4-fluorophenyl)-6-aminoquinoxaline,
2-(4-fluorophenyl)-6-acetamidoquinoxaline,
[2-(4-methoxyphenyl)-6,7-dimethoxyquinoxaline,]
2-phenethyl-6,7-diethoxyquinoxaline, 2-phenyl-6,7-dicarboxyquinoxaline,

[2-(4-methoxyphenyl)-6,7-dimethoxyquinoxaline,] or an N-oxide or a pharmaceutically acceptable salt thereof.

10. A compound selected from:

2-(thien-3-yl)quinoxaline,

[2-(thien-3-yl)-6,7-dimethylquinoxaline, 2-(thien-3-yl)-6,7,-dimethoxyquinoxaline, 2-(thien-3-yl)-6,7,-diethoxyquinoxaline,]

2-(5-chlorothien-3-yl)-6,7,-diethoxyquinoxaline, 2-(5-chlorothien-3-yl)-6,7,-dimethoxyquinoxaline, 2-(5-fluorothien-3-yl)-6,7,-diethoxyquinoxaline, 2-(thien-2-yl)-6,7,-diethoxyquinoxaline, 2-(thien-2-yl)-6,7,-dimethoxyquinoxaline, 2-(thien-2-yl)-6,7-dicarboxyquinoxaline or an N-oxide or a pharmaceutically acceptable salt thereof.

11. A compound according to claim 9 which is 2-phenyl-6,7-dimethylquinoxaline or a pharmaceutically acceptable salt thereof.

12. A compound according to claim 10 which is 2-(thien-2-yl)-6,7-diethoxyquinoxaline or a pharmaceutically acceptable salt thereof.

13. A compound according to claim 10 which is 2-(thien-2-yl)-6,7dimethoxyquinoxaline or a pharmaceutically acceptable salt thereof.

14. A compound according to claim 10 which is 2-(thien-3-yl)quinoxaline or a pharmaceutically acceptable salt thereof.

15. A compound according to claim 9, which is 2-(4-fluorophenyl)-6,7-diethoxyquinoxaline or a pharmaceutically acceptable salt thereof.

16. A compound according to claim 9 which is 2-(4-fluorophenyl)-6,7-dimethoxyquinoxaline or a pharmaceutically acceptable salt thereof.

17. A compound according to claim 9 which is 2-(4-fluorophenyl)-6-acetamidoquinoxaline or a pharmaceutically acceptable salt thereof.

18. A compound according to claim 9 which is 2-phenethyl-6,7-diethoxyquinoxaline or a pharmaceutically acceptable salt thereof.

19. A compound according to claim 9 which is 2-phenyl-6,7-dichloroquinoxaline or a pharmaceutically acceptable salt thereof.

20. A compound according to claim 10 which is 2-(5-fluorothien-2-yl)-6,7-diethoxyquinoxaline or a pharmaceutically acceptable salt thereof.

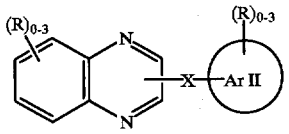

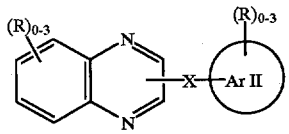

* * * * *